(12) United States Patent
Tjølsen et al.

(10) Patent No.: US 12,320,343 B2
(45) Date of Patent: Jun. 3, 2025

(54) ARRANGEMENTS AND METHODS FOR AVOIDING SPREADING OF INFECTIOUS AGENTS AND IMPROVING ELECTRIC SAFETY AND SUCTION PERFORMANCE OF A MEDICAL ASPIRATOR

(71) Applicant: EXCITUS MEDICAL AS, Tromsdalen (NO)

(72) Inventors: Øyvind Tjølsen, Stavanger (NO); Terje Bondhus, Stavanger (NO); Per Reidar Ørke, Hafrsfjord (NO)

(73) Assignee: EXCITUS MEDICAL AS, Tromsdalen (NO)

( * ) Notice: Subject to any disclaimer, the term of this patent is extended or adjusted under 35 U.S.C. 154(b) by 461 days.

(21) Appl. No.: 17/344,668

(22) Filed: Jun. 10, 2021

(65) Prior Publication Data

US 2021/0299346 A1    Sep. 30, 2021

Related U.S. Application Data

(63) Continuation of application No. 15/759,252, filed as application No. PCT/EP2015/070767 on Sep. 10, 2015, now Pat. No. 11,052,178.

(51) Int. Cl.
*F04B 35/04*    (2006.01)
*A61M 1/00*    (2006.01)

(52) U.S. Cl.
CPC .............. *F04B 35/04* (2013.01); *A61M 1/631* (2021.05); *A61M 1/74* (2021.05); *A61M 1/7413* (2021.05);

(Continued)

(58) Field of Classification Search
CPC ........ A61M 1/00; A61M 27/00; A61M 1/631; A61M 1/74; A61M 1/7413; A61M 1/784;

(Continued)

(56) References Cited

U.S. PATENT DOCUMENTS 4,705,504 A    11/1987 Viers
4,726,745 A *   2/1988 Adahan ................. F04B 53/00
                                                417/423.2

(Continued)

FOREIGN PATENT DOCUMENTS

CN          1571883 A    1/2005
CN        101378795 A    3/2009

(Continued)

OTHER PUBLICATIONS

International Search Report for related International Application No. PCT/EP2015/070767 dated Sep. 1, 2016.

(Continued)

*Primary Examiner* — Jessica Arble
(74) *Attorney, Agent, or Firm* — Renner, Otto, Boisselle & Sklar, LLP

(57) ABSTRACT

Vacuum pump (18) for a medical aspirator (10), the pump (18) comprising a tubular member (20); a piston (22) slidably arranged within the tubular member (20); a piston rod (24) connected to the piston (22); and a coupling mechanism (36) for detachably and functionally connecting the piston rod (24) to a motor (38) for driving the pump (18), wherein the piston rod (24) is configured to reciprocate linearly during operation of the pump (18).

7 Claims, 7 Drawing Sheets

(52) U.S. Cl.
CPC .............. *A61M 1/784* (2021.05); *A61M 1/81* (2021.05); *A61M 1/71* (2021.05); *A61M 1/743* (2021.05); *A61M 2205/8206* (2013.01); *A61M 2205/8262* (2013.01)

(58) Field of Classification Search
CPC .......... A61M 1/81; A61M 1/71; A61M 1/743; A61M 2205/8206; A61M 2205/8262; A61M 1/82; A61F 13/00; A61F 13/02; A61F 15/00; F04B 35/04; F04B 35/06
See application file for complete search history.

(56) References Cited

U.S. PATENT DOCUMENTS

| | | | |
|---|---|---|---|
| 4,781,707 | A | 11/1988 | Boehringer et al. |
| 6,520,931 | B2 | 2/2003 | Suh |
| 6,539,549 | B1 | 4/2003 | Peters, Jr. |
| 6,640,556 | B2 | 11/2003 | Ursan et al. |
| 7,284,965 | B2 | 10/2007 | Adahan |
| 8,317,774 | B2 | 11/2012 | Adahan |
| 8,323,264 | B2 * | 12/2012 | Weston ................. A61M 1/743 604/9 |
| 2003/0040687 | A1 | 2/2003 | Boynton et al. |
| 2007/0135779 | A1 * | 6/2007 | Lalomia ................. A61M 1/60 604/319 |
| 2008/0179344 | A1 | 7/2008 | Michaels et al. |
| 2009/0036873 | A1 | 2/2009 | Nielsen et al. |
| 2009/0157016 | A1 | 6/2009 | Adahan |
| 2010/0063483 | A1 | 3/2010 | Adahan |
| 2010/0298783 | A1 | 11/2010 | Chang |
| 2011/0015589 | A1 | 1/2011 | Svedman et al. |
| 2011/0218383 | A1 | 9/2011 | Broen et al. |
| 2012/0123360 | A1 * | 5/2012 | Locke ..................... A61M 1/88 604/319 |
| 2012/0259299 | A1 * | 10/2012 | Ryu ........................ A61M 1/96 604/319 |
| 2012/0271256 | A1 | 10/2012 | Locke et al. |

FOREIGN PATENT DOCUMENTS

| | | |
|---|---|---|
| CN | 101678155 A | 3/2010 |
| CN | 202516059 U | 11/2012 |
| DE | 1566561 A1 | 12/1969 |
| JP | 61-218787 | 9/1986 |
| JP | 2002-058737 | 2/2002 |
| JP | 200379718 A | 3/2003 |
| JP | 2005-500455 A | 1/2005 |
| JP | 2008167772 A | 7/2008 |
| JP | 2009-502301 | 1/2009 |
| JP | 2009-525086 A | 7/2009 |
| JP | 2010-525916 | 7/2010 |
| WO | 9605873 A1 | 2/1996 |
| WO | 03016719 | 2/2003 |
| WO | 2007/087809 A1 | 8/2007 |
| WO | 2009004369 A1 | 1/2009 |
| WO | 2013180502 A1 | 5/2012 |

OTHER PUBLICATIONS

International Preliminary Report on Patentability for related International Application No. PCT/EP2015/070767 dated Mar. 13, 2018.
Office Action for corresponding Eurasian Application No. 201890542 dated Jun. 11, 2019 and its English translation.
Office Action for corresponding Japanese Application No. 2018-532504 dated Aug. 27, 2019 and its English translation.
Office Action for corresponding Eurasian Application No. 201890542 dated Feb. 10, 2020 and its English partial translation.
Office Action for corresponding Chinese Application No. 201580084000.7 dated Apr. 7, 2020 and its English translation.
Office Action for corresponding Japanese Application No. 2018532504 mailed Apr. 21, 2020 and its English translation.
Office Action for corresponding European Application No. 15762615.1 dated Jun. 8, 2020.
Office Action for corresponding Australian Application No. 2015408663 dated Jun. 12, 2020.
Office Action for corresponding Eurasian Application No. 201890542 dated Oct. 6, 2020 and its Machine Translation.
Decision to Dismiss Amendment for corresponding Japanese Patent Application No. 2018-532504 dated Dec. 15, 2020 and its Machine Translation.
Decision of Refusal for corresponding Japanese Patent Application No. 2018-532504 dated Dec. 15, 2020 and its Machine Translation.
Second Office Action for corresponding Chinese Patent Application No. 201580084000.7 dated Dec. 24, 2020 and its English Translation.
Allowed claims of related U.S. Appl. No. 15/759,252, filed Mar. 12, 2018.
Third Office Action for corresponding Chinese Application No. 201580084000.7 dated Jul. 5, 2021 and its English translation.
Office Action for corresponding Canadian Application No. 2,997,832 dated Oct. 28, 2021.
Office Action for corresponding Chinese Application No. 201580084000.7 dated Oct. 9, 2021 and its English translation.
Examination Report for corresponding Australian Application No. 2021203773 dated Jan. 18, 2022.
Office Action for corresponding Japanese Application No. 2021-063991 dated May 10, 2022 and its English Translation.

* cited by examiner

ARRANGEMENTS AND METHODS FOR AVOIDING SPREADING OF INFECTIOUS AGENTS AND IMPROVING ELECTRIC SAFETY AND SUCTION PERFORMANCE OF A MEDICAL ASPIRATOR

TECHNICAL FIELD

The present disclosure generally relates to the avoidance of spreading infectious agents and the improvement of electric safety and suction performance, especially in the context of a medical aspirator. In particular, various vacuum pumps for a medical aspirator, a motor unit for a medical aspirator, a disposable arrangement, an arrangement for inactivating infectious agents in an air stream, such as an air stream within a medical aspirator, a two-stage canister for a medical aspirator, an aspiration hose for a canister of a medical aspirator and medical aspirators including these features are provided. A method for controlling the vacuum generated by a vacuum pump is also provided.

BACKGROUND

A medical aspirator, also referred to as a medical suction unit, is a common device for removing e.g. bodily fluids during medical procedures or emergency situations. For example, a patient or victim may need to be exposed to vacuum suction to remove bodily fluids and secretions from the lungs or other locations. A medical aspirator is a part of the standard equipment in most ambulances.

WO 9421312 A2 discloses a portable aspirator with a vacuum pump and a fluid container arranged within a housing. The pump generates a reduced pressure within the container, enabling fluid to be suctioned from a patient with an aspiration hose and stored within the container. A filter is connected between the vacuum hose and a connector grommet removably mounted in an access hole in the housing. The container is disconnected from the vacuum hose to flush the aspirator between uses.

During use of the aspirator, there is a risk that secretions from the patient deteriorate the functioning of the filter and infectious agents might spread to the pump and the driving electronics. Consequently, the filter might no longer function to galvanically separate the patient from the driving electronics. Since the secretions are often electrically conductive, the patient and the operator risk receiving an electroshock.

Moreover, infectious agents might stick to other parts of the aspirator and risk to spread infections. The necessary cleaning and sterilization procedures between uses also become complicated and it is therefore difficult to control the cleanliness of the aspirator.

A further drawback with the portable aspirator in WO 9421312 A2 is that the air pumped out to the atmosphere (the exhaust air) might contain infectious agents, in particular when the filter function is deteriorated. This exposes personnel and patients in vicinity of the aspirator to a health risk. Also the risk of contaminants adhering to sterile tools, surfaces etc. around the aspirator is increased.

SUMMARY

Accordingly, one object of the present disclosure is to provide arrangements and methods for avoiding the spreading of infectious agents and improving electric safety, in particular in connection with a medical aspirator. Moreover, one object of the present disclosure is to provide reliable galvanic barriers within a medical aspirator. Further objects are to provide solutions improving the performance of and simplifying the structure of a medical aspirator.

According to one aspect, a vacuum pump for a medical aspirator is provided, where the pump comprises a tubular member, a piston slidably arranged within the tubular member, a piston rod connected to the piston, and a coupling mechanism for detachably and functionally connecting the piston rod to a motor for driving the pump, wherein the piston rod is configured to reciprocate linearly during operation of the pump.

The tubular member may be constituted by a cylinder. Due to the linearly reciprocating movement of the piston rod, the requirements for tolerances between the tubular member and the piston can be reduced, thus making it simpler and cheaper to manufacture. Also, a pump unit, e.g. a housing for the pump, can be made more compact.

Since the vacuum pump can be attached to and detached from the motor, the vacuum pump may be made disposable, i.e. made with a rather simple structure and made from a cheap material, e.g. plastics. Thus, the pump may be a single use pump. The coupling mechanism may be a "quick coupling". The coupling mechanism may adopt various forms, such as a connection with threads, latches, wedges etc.

The vacuum pump may comprise two one-way valves, one valve for delivering air from a piston chamber within the tubular member to the atmosphere, optionally via an exhaust channel, and one valve for delivering air from a vacuum channel into the piston chamber.

The vacuum pump may be integrally formed with a disposable canister. Alternatively, the vacuum pump may be attachable to a disposable canister. With this variant, there can be provided a disposable set including one disposable pump and one or a plurality of, for example five, disposable canisters. Hospitals and similar institutions using medical aspirators may thus subscribe to such disposable sets.

The vacuum pump may further comprise a drive mechanism configured to translate a rotary motion of the motor to the linearly reciprocating motion of the piston rod and the coupling mechanism may be provided on the drive mechanism. For this drive, the motor may comprise a rotatable motor shaft.

The rotary motion from the motor may be a rotary motion of a separate shaft driven by an output shaft of the motor, e.g. by means of a belt transmission. In this manner, noise can be reduced and the requirement for tolerances of the motor mounting can be lowered. However, the linear reciprocation of the piston rod may also be accomplished by transferring a linear motion from a linear motor.

When the coupling mechanism is configured to establish a detachable coupling between the drive mechanism and the motor, both the drive mechanism and the pump can be made disposable. In this case, a coupling mechanism on the piston rod may be omitted.

The drive mechanism may comprise a first arm, a second arm pivotally connected to the first arm and a guiding arrangement for linearly guiding the first arm along with the linearly reciprocating motion of the piston rod. The guiding arrangement may be constituted by a linear bearing.

The first arm may be constituted by the piston rod, or may be fixedly attached to the piston rod. In case the first arm is constituted by the piston rod, the guiding arrangement may be configured to linearly guide the piston rod in the linearly reciprocating motion.

The drive mechanism may alternatively be attached with a coupling mechanism connected to an eccentric on the motor shaft. The second arm may thus constitute an eccentric rod. Thus, the drive mechanism may resemble a classic locomotive drive. The eccentric may alternatively be referred to as a base plate or a flywheel.

Alternatively, the drive mechanism may comprise a track member with a track extending substantially perpendicular to the directions of reciprocation of the piston rod. By guidingly receiving a pin from the motor shaft (offset with respect to a rotational axis of the motor shaft) in the track, the track member reciprocates linearly along with the piston rod as the motor shaft rotates. The track member may be slidingly supported within a frame with two inwardly facing grooves.

Although the drive mechanism has been described above as being driven by the motor shaft, it is also possible to arrange a rotatable intermediate shaft driven by the motor shaft via a belt member. The belt member may reduce (gear down) the rotational speed of the intermediate shaft in view of the motor shaft. Thus, a drive mechanism described as being driven by a motor shaft in the present disclosure may also be driven by such intermediate shaft. Further alternative configurations to drive the drive mechanism by the motor shaft are also conceivable.

The vacuum pump may further comprise a membrane fixed to the piston rod for sealingly closing the pump, e.g. sealingly closing one region of the pump, such as one side of the pump or a partial area on one side of the pump. The membrane may be flexible and may alternatively be referred to as a diaphragm.

The membrane thereby follows the linearly reciprocating movement of the piston rod. The linearly reciprocating motion is less harmful to the membrane than reciprocating motions of piston rods moving with varying angles during their reciprocation.

Since the membrane sealingly closes the pump, the membrane constitutes a galvanic barrier. In case a filter is used (for example in a canister unit), the filter may constitute a first galvanic barrier and the membrane may constitute a second galvanic barrier.

The membrane may constitute a wall of the pump. The membrane may be a gore layer or a PTFE (polytetrafluoroethylene) membrane.

According to a further aspect, a vacuum pump for a medical aspirator is provided, where the pump comprises a tubular member, a piston slidably arranged within the tubular member, a piston rod connected to the piston, and a membrane fixed to the piston rod for sealingly closing the pump, wherein the piston rod is configured to reciprocate linearly during operation of the pump. This pump may be configured both as disposable and non-disposable (i.e. permanently attached to a motor unit of the medical aspirator). The membrane may sealingly close one region of the pump.

According to a further aspect, a motor unit for a medical aspirator is provided, where the motor unit comprises a motor for driving a vacuum pump, at least two batteries, where each battery is configured to supply drive current to the motor, a relay associated with each battery, wherein each relay is configured to operate between an allowing state for receiving a charge from a mains power supply, and a non-allowing state in which the charge from the mains power supply is not allowed. The batteries may be of any suitable type, for example lead-acid batteries. The batteries and the relays may be arranged within a power distribution unit of the motor unit.

The mains power supply may be a power supply from a building (e.g. a hospital) or from a vehicle (e.g. an ambulance). The mains power supply may be 12 V DC. The relays of the batteries may be galvanically separated from each other.

The motor unit may further comprise a control unit configured to control the at least two batteries to alternatingly supply drive current to the motor. More specifically, the control unit may be configured to alternatingly control the relays such that the relay of the battery that currently supplies drive current to the motor adopts the non-allowing state and the relay of each one or more remaining batteries adopt the allowing state so that the motor is never electrically connected to the mains power supply. In this way, the relays constitute a third galvanic barrier.

Thus, in case two batteries are used, one battery is being charged and the other battery delivers a drive current during operation of the motor unit. With this control, the motor unit can be safely connected to the mains power supply (e.g. in an ambulance) during a suction operation of the medical aspirator.

According to a further aspect, a medical aspirator is provided, where the medical aspirator comprises a vacuum pump according to the present disclosure and/or a motor unit according to the present disclosure.

Each medical aspirator according to the present disclosure may comprise a canister. The canister may be attached to the pump unit or pump such that the pump can establish a vacuum within the canister. The medical aspirator may also comprise an aspiration hose attached to the canister. Thus, by generating a reduced pressure within the canister, fluids and secretions can be suctioned from a patient with the aspiration hose and collected within the canister.

The medical aspirator may also comprise a filter for removing infectious agents, such as bacteria. The filter may be arranged within a channel between the canister and the pump. For example, the filter may be arranged in a vacuum channel within a canister unit (e.g. a canister housing). The filter may be a HEPA filter. The canister or the canister unit may also be disposable.

Throughout the present disclosure, the pump unit may be integrally formed with the canister or the canister unit. Alternatively, these parts may be detachably connectable to each other.

According to a further aspect, a disposable arrangement is provided, where the disposable arrangement comprises a first disposable part connectable to a second part, or forming a joint structure together with the second part, a flexible enclosure configured to provide a protective shield around the second part during use of the first disposable part together with the second part, and configured to be inverted to provide a protective shield around the first disposable part after completion of the use, or during pauses of the use.

The disposable arrangement can be used in a wide range of applications where a "dirty" component should be protected. The protective shield may constitute a bacterial shield, a chemical shield, a gas shield and/or a dirt shield. As one example, the disposable arrangement may be implemented in a paint brush where the brush constitutes the first disposable part and the shaft constitutes the second part.

In case the brush is detachably connectable to the shaft, the flexible enclosure may be provided on the brush which is then connected to the shaft. The flexible enclosure may then be wrapped around the shaft of the paint brush for protecting the shaft, and preferably also the painter's hand, during painting. By inverting the flexible enclosure to cover the brush, the brush can be prevented from drying and the shaft is clean since it has been protected by the flexible enclosure during the painting procedure. The flexible enclosure can also be filled with detergents, solvents, gases, inhibitors or other relevant substances/fluids in the inverted state. The brush with the flexible enclosure wrapped around may be detached from the shaft and discarded or stored. The assembly does in this manner not spread any dirt, in this case mainly paint.

The disposable arrangement may also be implemented in a paint brush where the brush is permanently attached to the shaft. The brush and the shaft thereby constitute a joint structure. The joint structure may thus be a disposable joint structure. The flexible enclosure may protect the shaft in the same manner as described above during a painting procedure. When finished, the flexible enclosure may be inverted to protect the brush and the entire paint brush (i.e. the joint structure) may be discarded or stored without spreading any dirt, i.e. paint.

One further conceivable application of the disposable arrangement is for spray cans. Within the present disclosure however, the disposable arrangement is mainly described in the context of a medical aspirator.

Thus, according to one variant, a pump unit for a medical aspirator is provided, where the pump unit comprises a vacuum pump drivable by a motor of a motor unit, a flexible enclosure configured to provide a bacterial shield around the motor unit during a suction operation of the medical aspirator, and configured to be inverted to provide a bacterial shield around the pump unit after completion of the suction operation of the medical aspirator.

The flexible enclosure may be a plastic bag. The flexible enclosure may comprise a closable opening which in an open condition allows the flexible enclosure to be inverted from a state enclosing the second part to a state enclosing the first disposable part and which in a closed condition forms a part of a substantially fluid tight seal around the second part and the first disposable part, respectively.

Thus, according to one variant for a pump unit for a medical aspirator, the flexible enclosure comprises a closable opening which in an open condition allows the flexible enclosure to be inverted from a state enclosing the motor unit to a state enclosing the pump unit and which in a closed condition forms a part of a substantially fluid tight (or fluid tight and air tight) seal around the motor unit and the pump unit, respectively.

When the flexible enclosure covers the motor unit, air trapped within the flexible enclosure may be suctioned, for example through the closable opening. It is thereby possible to establish a tight fit of the flexible enclosure to the exterior of the motor unit, for example to facilitate operation of a user interface on the motor unit. The tight fit of the flexible enclosure on the motor unit also indicates that the protective shield is intact. The closable opening may be constituted by a zip-lock, or by two zip-locks, where one zip-lock is used to close the opening when the flexible enclosure covers the first disposable part and one zip-lock is used to close the opening when the flexible enclosure covers the second part.

In case the disposable arrangement is used in the context of a medical aspirator, the first disposable part is constituted by a pump unit with a vacuum pump for a medical aspirator, the second part is constituted by a motor unit with a motor for the medical aspirator, where the vacuum pump is drivable by the motor, and the flexible enclosure is configured to provide a bacterial shield around the motor unit during a suction operation of the medical aspirator, and configured to be inverted to provide a bacterial shield around the pump unit after completion of the suction operation of the medical aspirator.

When the flexible enclosure covers the motor unit (the second part), the enclosure may be said to be in a ready mode or an operational mode. When the flexible enclosure covers the pump unit (the first disposable part), the enclosure may be said to be in a disposal mode. Thus, the flexible enclosure first protects the motor unit (in the ready mode) and then protects the operator (in the disposal mode).

The flexible enclosure may additionally be configured to be inverted to provide a bacterial shield around the pump unit and a canister unit (also including an aspiration hose) after completion of the suction operation of the medical aspirator.

Before and during use of the medical aspirator, when the flexible enclosure encloses the motor unit, a user interface (e.g. buttons and/or control knobs) can be operated through the flexible enclosure, e.g. by pushing on the flexible enclosure. Upon completion of the suction operation, an operator may invert the flexible enclosure such that it encloses the pump unit (optionally also the canister unit). Before closing the flexible enclosure, the operator may also throw used gloves into the flexible enclosure.

The flexible enclosure may be configured to provide a fluid tight seal around the motor unit and the pump unit in the ready mode and in the disposal mode, respectively. This fluid tight seal may additionally be air tight.

The vacuum pump may comprise a membrane and the flexible enclosure may be integrally formed with the membrane. Thereby, the flexible enclosure and the membrane form one continuous part. The membrane may be the same membrane as described above, e.g. fixed to a disposable piston rod for sealingly closing one region of the pump.

According to a further aspect, a medical aspirator is provided, where the medical aspirator comprises a disposable arrangement with a pump unit and a pump according to the present disclosure, and a motor unit comprising a motor for driving the vacuum pump of the pump unit. The pump unit may be detachably connectable to the motor unit.

According to a further aspect, there is provided an arrangement for inactivating infectious agents (e.g. bacteria) in an air stream, such as an air stream within a medical aspirator, where the arrangement comprises a channel for guiding an air stream therethrough, the channel being at least partly constituted by a material permeable to ultraviolet light, an ultraviolet light source arranged adjacent to the channel configured to expose the air stream within a treating section of the channel to ultraviolet (UV) light.

The ultraviolet light source may be configured to provide UV type C (UVC) light with a wavelength of 200 to 280 nm, such as a wavelength of 250 to 280 nm, such as 265 nm. The channel may be designed such that the entire air stream is exposed to ultraviolet light during a given time, i.e. designed in dependency of the flow rate within a channel of a particular application. The channel may be a vacuum or exhaust channel within the medical aspirator.

However, this arrangement may also be used in a wide range of other applications, including ventilation arrangements in vehicles (cars, buses, trains, airplanes), medical facilities, patient tents, isolation wards, incubators, etc., where the inlet air can be subjected to ultraviolet light from the ultraviolet light source. Further possible application for this arrangement include surgical masks (such as surgical antibacterial masks of the gas mask type) for medical personnel, face masks with assisted ventilation (respirators, cardiopulmonary resuscitation (CPR) masks, etc.) where the ultraviolet light source may be provided to expose the connecting hose to ultraviolet light, breathing bags, CPR training manikins etc.

The arrangement may further be used to protect persons with suppressed immune systems, e.g. after cancer treatment, against infections. The ultraviolet light source may be carried by a person, for example in a backpack or with a belt, and the channel may be constituted by a hose between the ultraviolet light source and a face mask. Thus, ambient air can be disinfected and high mobility can be provided for the person carrying the arrangement.

The arrangement may further be implemented as a universal portable device configured to be detachably attached to, e.g. clamped on, hoses of varying widths and of any type, i.e. for any application. As an example, the arrangement may be implemented as a clamp-on device containing a battery package and the ultraviolet light source that can be clamped onto a hose. The clamp-on device may be designed with two pieces, each of a generally half-cylinder appearance, containing or constituting the battery package and the ultraviolet light source, respectively. The two pieces may be hingedly connected to each other, optionally with a biasing mechanism biasing the two pieces on the hose. Alternatively, or in addition, a strap may be provided to secure the pieces to the hose.

Moreover, the ultraviolet light source may be arranged within a device to which one or several hoses can be detachably connected. Such device may be portable or stationary. The device may have an opening for drawing in ambient air. Alternatively, the device may be coupled to an inlet hose, i.e. be arranged between two hoses.

The ultraviolet light source may for example be a LED (light-emitting diode) light source, a laser, a pulsed laser, a pulsed xenon or a pulsed LED. In case the arrangement is used in connection with a medical aspirator, the ultraviolet light source may be positioned at any suitable location for exposing the air stream within the treating section to ultraviolet light. For example, the ultraviolet light source may be positioned at the exterior (e.g. configured as a box on top of), or close to the exterior of the pump unit or the motor unit. Thus, the arrangement allows retrofitting on existing medical aspirators.

The ultraviolet light source may also be arranged to expose air within the canister to ultraviolet light. Since the air is moving through the canister, the canister may be said to constitute a channel. Fluids and secretions collected inside the canister may also be exposed to the ultraviolet light to be disinfected.

The channel within the treating section may comprise at least two channel segments configured to direct the air stream in different directions. As an example, the treating section may include two substantially parallel channel segments and an interconnecting bend. As further examples, the channel within the treating section may be arranged as a spiral, coil or helix and/or may comprise a plurality of substantially parallel channel segments.

According to a further aspect, there is provided a medical aspirator comprising an arrangement for inactivating infectious agents in an air stream according to the present disclosure.

According to a further aspect, there is provided a method for controlling the vacuum generated by a vacuum pump driven by a motor in a medical aspirator, where the method comprises detecting the generated vacuum, and controlling the drive current supplied to the motor based on the detected generated vacuum.

According to one variant, the drive current supplied to the motor is controlled to be linearly proportional to the detected generated vacuum. In this case, a relatively high drive current is supplied to the motor when the generated vacuum is low and a relatively low drive current is supplied to the motor when the generated vacuum is high. The motor may be configured to provide a rotational moment (torque) that is proportional to the drive current. The motor may be a BLDC (brushless DC electric) motor.

Depending on the particular medical procedure, patient condition, or other factors, it is often preferable to control the level of vacuum to which the patient is exposed and to set a maximum limit of such vacuum level. For example, a patient might be harmed if the aspiration hose sticks within the oral cavity. By controlling the drive current supplied to the motor in this manner, the maximum vacuum in an aspiration hose can be limited to a specified threshold.

According to a further aspect, a medical aspirator is provided, where the medical aspirator comprises a vacuum pump, a motor configured to drive the vacuum pump, means for detecting the generated vacuum, and a control unit configured to control the drive current supplied to the motor according to the present disclosure. The vacuum level generated by the motor may be derived in various manners. When operating a BLDC motor, the generated vacuum is proportional to the drive current. However, a dedicated vacuum sensor of known type may also be used to detect the generated vacuum. The medical aspirator according to the present disclosure may additionally comprise a mechanical vacuum regulator, for example arranged within the pump unit.

According to a further aspect, a two-stage canister for a medical aspirator is provided, where the canister comprises a first reservoir with an inlet for an aspiration hose and an outlet for a vacuum channel, a second reservoir, and a partition member movable from a closed position, where the partition member is configured to maintain a fluid within the first reservoir, to a drain position in order to drain the fluid within the first reservoir to the second reservoir.

The drain position may or may not be an open position where a fluid communication is established between the second reservoir and the inlet/outlet of the first reservoir. When the partition member is in the closed position, the second reservoir is functionally isolated from the first reservoir in terms of vacuum build-up (the term "partition member" is selected since this member partitions the first reservoir and the second reservoir in the closed position). Thus, the effective volume for vacuum buildup in the canister is reduced when the partition member is in the closed position since vacuum only has to be established within the first reservoir and not also within the second reservoir.

As a consequence, the time for vacuum build-up can be reduced. This is useful since the maximum capacity of many canisters is sometimes never used or only used occasionally. Moreover, if the canister is to be cleaned, the volume required to clean is reduced if the second reservoir has not been used. Also, the first reservoir can be disposed without disposing the second reservoir, which will keep costs down.

After some time of suction operation with the medical aspirator, the first reservoir may be full, or nearly full, or it may be desired to empty the first reservoir for other reasons, for example for hygienic reasons. By maneuvering the partition member from the closed position to the drain position, a fluid communication may open between the first reservoir and the second reservoir. Thereby, fluids and secretions within the first reservoir can be drained to the second reservoir by gravity.

Throughout the present disclosure, the first reservoir and the second reservoir may alternatively be referred to as a first chamber and a second chamber, respectively, or as a first stage canister and a second stage canister, respectively. The second reservoir may have a larger volume than the first reservoir. The first reservoir may have a volume of 200 ml to 400 ml, such as 300 ml. The second reservoir may have a volume of 600 ml to 800 ml, such as 700 ml.

The two-stage canister may be disposable. Alternatively, or in addition, it may be formed integrally with or may be detachably attachable to a pump, such as a disposable pump.

The two-stage canister may be comprised in a canister unit as described in the present disclosure. A filter may be provided in the vacuum channel. The canister unit may further comprise the aspiration hose and/or the vacuum channel. As mentioned above, fluids and secretions can be suctioned from a patient with the aspiration hose and collected within the canister by generating a reduced pressure within the canister.

Both the first reservoir and the second reservoir may be configured to withstand a reduced pressure during operation of the two-stage canister with the partition member in the drain position. In other words, both the first reservoir and the second reservoir may be designed to withstand vacuum build-up. With this configuration, the two-stage canister can also be operated as a one-stage canister when the partition member adopts the drain position, i.e. it can be operated with a large continuous volume formed by both the first reservoir and the second reservoir.

The second reservoir may be flexible. Consequently, the space occupied by the second reservoir may be reduced. That is, the second reservoir may expand based on the volume of the fluid drained into the second reservoir.

The partition member may be movable from the drain position to the closed position. In other words, the partition member may be reversibly movable between the closed position and the drain position. In this manner, the two-stage canister can repeatedly run with a reduced volume (i.e. with the partition member in the closed position) with one or several emptying procedures (i.e. with the partition member in the drain position) between the repeated runs.

For all variants where the partition member is movable from the drain position to the closed position, the partition member may be biased towards the closed position. This may for example be realized with a suitable spring arrangement.

However, the partition member may alternatively be irreversibly movable from the closed position to the drain position. This may be beneficial in case a simplified design is sought, such as for disposable two-stage canisters.

The partition member may comprise a closing piston for sealingly closing the first reservoir to the second reservoir when the partition member is in the closed position. For example, the first reservoir may be constituted by a tubular member. In the closed position of the partition member, the piston may abut against the rim of the tubular member, i.e. the piston may be larger than the interior profile of the tubular member. Alternatively, the piston may be received within the tubular member when the partition member is in, or adopts, the closed position. Naturally, the outer profile of the piston thereby corresponds to the interior profile of the tubular member. These profiles may be circular, square, etc.

The partition member may comprise a piston rod attached to the closing piston and the piston rod may extend through the exterior of the first reservoir. With this design, the part of the piston rod extending through the exterior of the first reservoir functions as a handle and may be actuated by an operator in order to maneuver the partition member from the closed position to the drain position and/or in the reverse direction.

The partition member may comprise a pressing piston for pressing the fluid within the first reservoir to the second reservoir during movement of the partition member from the closed position to the drain position. In this manner, immediate fluid communication between the second reservoir and the inlet/outlet can be prevented. In addition, viscous fluids and/or secretions are more reliably drained since they are pushed from the first reservoir into the second reservoir. Thus, with this variant, it is not needed to rely on gravity for draining the first reservoir to the second reservoir.

According to a further aspect, a medical aspirator comprising a two-stage canister according to the present disclosure is provided.

Some prior art aspiration hoses for medical aspirators are delivered with, or have as an option, an air inlet at the tip (distal section). An operator can disrupt the vacuum generated inside the aspiration hose by lifting the thumb off the air inlet and let air from the atmosphere enter the aspiration hose. This may be desired when the aspiration hose sticks to human tissue in the suction region. The function is analogous to the function of the valve commonly provided on shafts for vacuum cleaners. In some other prior art aspiration hoses, the only way to relieve the vacuum inside the aspiration hose when it sticks to human tissue is to detach the aspiration hose from the canister.

According to a further aspect, an aspiration hose for suctioning fluids from a patient into a canister of a medical aspirator is provided, where the aspiration hose comprises an upstream section, a downstream section, and a valve mechanism switchable between an open position and a blocking position, wherein the valve mechanism is configured to allow the suctioned fluids to pass from the upstream section to the downstream section in the open position, and to block the suctioned fluids in the upstream section from entering the downstream section in the blocking position.

When the valve mechanism is in the blocking position and a pump of the medical aspirator is running, vacuum is generated in the downstream section but not in the upstream section. With the method for controlling the vacuum generated by a vacuum pump driven by a motor in a medical aspirator as described herein, the pump will stop when a desired vacuum set point is reached. Thereby, the valve mechanism of the aspiration hose can be used as an on/off actuator for a vacuum pump. This is useful since medical suction (aspiration) is normally performed in short time intervals. Additionally, by controlling the vacuum pump with the valve mechanism, the vacuum pump of the medical aspirator can be stopped without any hazzle, batteries can be saved and the noise can be reduced.

The valve mechanism may also be configured to be positioned in one or several intermediate positions between the blocking position and the open position. By positioning the valve mechanism in an intermediate position, the operator can adjust the airflow.

The canister and/or the medical aspirator may be of any type described herein. For example, the entire aspiration hose may be made of disposable plastics. The upstream section and the downstream section may alternatively be referred to as a distal section and a proximal section, respectively. A distal section of the aspiration hose is closer to the patient subjected to medical suction and the proximal section is closer to the canister of the medical aspirator. The upstream section may be constituted by a section immediately downstream of a suction opening at a distal end of the aspiration hose.

The term "blocking position" of the valve mechanism is selected to indicate a substantial blocking of the suctioned fluids. In case all fluid is blocked, the blocking position may also be referred to as a closing position. Throughout the present disclosure, the blocking position and the open position may alternatively be referred to as a passive position and an active position, respectively.

The valve mechanism may have a variety of designs in order to accomplish the switching between the open position and the blocking position. As one example, the valve mechanism comprises a valve member with an opening part and a closing part. By aligning the closing part with a main channel inside the aspiration hose, the valve mechanism adopts the blocking position. Similarly, by aligning the opening part with the main channel inside the aspiration hose, the valve mechanism adopts the open position. The valve member of the valve mechanism may be guided inside a valve mechanism housing to move between the blocking position and the open position.

The aspiration hose may further comprise a biasing member configured to bias the valve mechanism into the blocking position. In this manner, the valve mechanism constitutes a normally-closed valve. According to one variant, the biasing member is constituted by a spring that pushes the valve mechanism from the open position to the blocking position. With this variant, the operator may push the valve mechanism from the blocking position into the open position as long as fluids are to be suctioned through the aspiration hose. A locking mechanism may be provided to lock the valve mechanism in the open position and/or in any intermediate position.

The aspiration hose may further comprise an air inlet for fluid communication between the upstream section and the atmosphere when the valve mechanism adopts the blocking position. The air inlet may establish the fluid communication through a wall of the aspiration hose in the upstream section. Such air inlet may be constituted by an opening. A dedicated closing mechanism may be associated with the opening to close the same. Alternatively, the valve mechanism may be arranged to also close this air inlet. In case no such closing mechanism is provided, the operator may still close the opening with a finger, e.g. the thumb.

The aspiration hose may be configured such that fluid communication between the upstream section and the atmosphere is closed when the valve mechanism adopts the open position. According to one variant, this is accomplished by arranging an air inlet channel between the upstream section and the atmosphere via a valve mechanism housing. In case the valve mechanism comprises a valve member with an opening part and a closing part, the opening part may be aligned with the main channel inside the aspiration hose and the closing part may be aligned with the air inlet channel when the valve mechanism adopts the open position. Thereby, the main channel is open and the air inlet channel is closed when the valve mechanism adopts the open position.

When this valve mechanism is moved from the open position to the blocking position, the closing part is moved from the air inlet channel to the main channel. Thereby, the main channel inside the aspiration hose is blocked and the air inlet channel is open when the valve mechanism adopts the blocking position. Corresponding intermediate positions of the opening part and the closing part with respect to the main channel and the air inlet channel are also conceivable, e.g. a positioning of the valve member such that both the main channel and the air inlet channel are approximately half open.

According to a further aspect, a canister comprising an aspiration hose according to the present disclosure is provided.

According to a further aspect, a medical aspirator comprising an aspiration hose according to the present disclosure is provided.

BRIEF DESCRIPTION OF THE DRAWINGS

Further details, advantages and aspects of the present disclosure will become apparent from the following embodiments taken in conjunction with the drawings, wherein.

DETAILED DESCRIPTION

Figure 1:
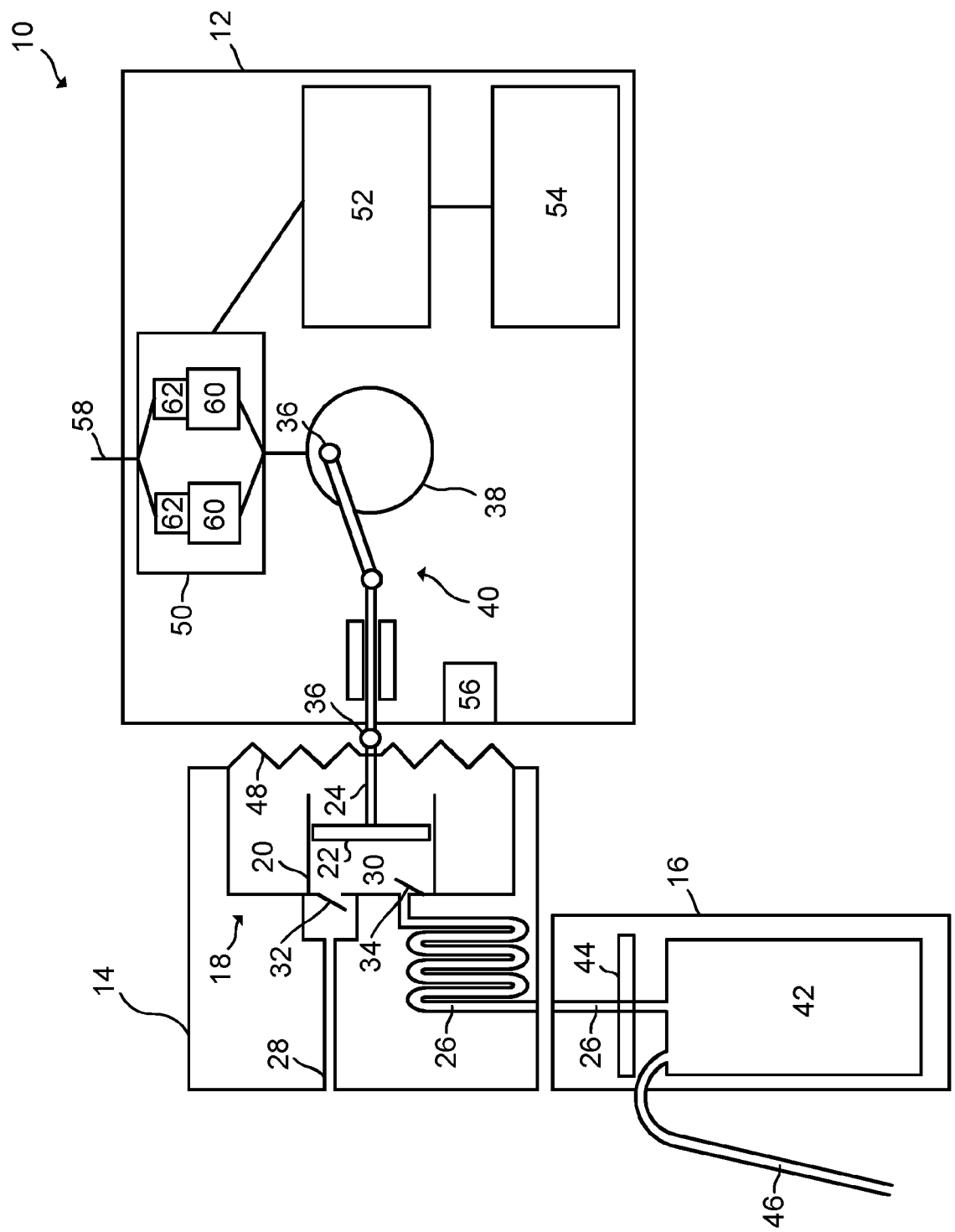
FIG. 1: schematically represents a medical aspirator comprising a motor unit, a pump unit and a canister unit.

In the following, various vacuum pumps for a medical aspirator, a motor unit for a medical aspirator, a disposable arrangement in the form of a pump unit for a medical aspirator, an arrangement for inactivating infectious agents in an air stream, such as an air stream within a medical aspirator, a two-stage canister for a medical aspirator, an aspiration hose for a canister of a medical aspirator and respective medical aspirators including these features will be described. The same reference numerals will be used to denote the same or similar structural features.

FIG. 1 schematically represents a medical aspirator 10 comprising a motor unit 12, a pump unit 14 and a canister unit 16.

The pump unit 14 is basically a housing enclosing a vacuum pump 18. The vacuum pump 18 comprises a tubular member 20, a piston 22 and a piston rod 24 connected to the piston 22. In FIG. 1, the piston 22 and the piston rod 24 are integrally formed. However, the piston 22 and the piston rod 24 may alternatively be formed separately.

The tubular member 20 is implemented as a cylinder in FIG. 1. The piston rod 24 is configured to reciprocate linearly during operation of the pump 18. Thus, also the piston 22 is configured to reciprocate linearly within the tubular member 20 during operation of the pump 18.

A vacuum channel 26 and an exhaust channel 28 are further provided at one side of a piston chamber 30 within the pump unit 14. As can be seen in FIG. 1, the pump 18 comprises two one-way valves (or check valves) 32, 34. One valve 34 is arranged to deliver air from the vacuum channel 26 into the piston chamber 30 and prevent air in the opposite direction. The other valve 32 is arranged to deliver air from the piston chamber 30 via the exhaust channel 28 to the atmosphere and prevent air in the opposite direction. By reciprocating the piston 22 within the tubular member 20, air is alternatingly suctioned into the piston chamber 30 and pressed out from the piston chamber 30 to suction air from the vacuum channel 26.

The vacuum pump 18 and all other components within the pump unit 14 are disposable. In FIG. 1, all these components are made of plastics.

The vacuum pump 18 further comprises a coupling mechanism 36 for detachable and functional attachment of the piston rod 24 to a motor 38 within the motor unit 12. As can be gathered from FIG. 1, the piston rod 24 is not attached immediately to the motor 38, but attached via a drive mechanism 40.

The drive mechanism 40 is configured to translate a rotary motion of the motor 38 (more specifically, a motor shaft) into a linearly reciprocating motion of the piston rod 24. However, the rotary motion from the motor 38 may alternatively be a rotary motion of a separate shaft driven by a motor shaft of the motor 38, e.g. by means of an intermediate belt transmission. The linear reciprocation of the piston rod 24 may also be accomplished by transferring a linear motion from a linear motor. Since the coupling mechanism 36 in FIG. 1 is attached between the piston rod 24 and the drive mechanism 40, the piston rod 24 is functionally connected to the motor 38.

The coupling mechanism 36 may adopt various forms. In FIG. 1, the coupling mechanism 36 is located between the piston rod 24 and the drive mechanism 40. However, the coupling mechanism 36 may alternatively be located between the drive mechanism 40 and the motor 38, as is also indicated by reference numeral "36" in FIG. 1. In this case, also the drive mechanism 40 may be made disposable, e.g. made of plastics. In this way, the pump 18 may comprise the drive mechanism 40.

The canister unit 16 constitutes a housing containing a canister 42. In FIG. 1, the canister unit 16 is illustrated as detachably attached to the pump unit 14. However, the canister unit 16 may alternatively be permanently attached to the pump unit 14 or integrally formed with the pump unit 14. In both cases, the canister 42 may be arranged detachably within the canister unit 16.

A vacuum channel 26 and a filter 44 are also provided within the canister unit 16. The vacuum channel 26 within the canister unit 16 is in fluid communication with the canister 42. Although the filter 44 in FIG. 1 is positioned within the canister unit 16, the filter 44 (or an additional filter) may be provided on the exhaust channel 28.

The filter 44 in FIG. 1 is a HEPA filter and serves to block infectious agents that have entered the vacuum channel 26, for example due to splashing within the canister 42. The filter 44 may be said to constitute a first galvanic barrier.

The respective vacuum channels 26 of the pump unit 14 and the canister unit 16 are in fluid communication with each other when the pump unit 14 is attached to the canister unit 16. Due to the vacuum generated by the pump 18, air is sucked from the canister 42 and into the vacuum channel 26.

The canister unit 16 further comprises an aspiration hose 46. In FIG. 1, the aspiration hose 46 is in an operational state, i.e. separated from the canister unit 16. Prior to use (and after use), the aspiration hose 46 may be attached to the exterior of the canister unit 16, e.g. by means of one or more clips. In the operational state, the aspiration hose 46 may be used to suction secretions from a patient into the canister 42.

The canister unit 16 is disposable. In FIG. 1, all components of the canister unit 16 are made of plastics. However, one or more alternative disposable materials may be used.

After a suction operation of the medical aspirator 10, the coupling mechanism 36 can be disengaged to remove the pump unit 14 and the canister unit 16 from the motor unit 12. Thus, the pump unit 14 and the canister unit 16 can be discarded. Consequently, any infectious agents collected within these parts are safely removed from the remainder of the medical aspirator 10.

Since the piston rod 24 reciprocates linearly during operation of the pump 18, also the piston 22 reciprocates linearly within the tubular member 20.

The tubular member 20 does thereby not need any clearance around the piston 22 to allow for angular variations of the piston rod 24 and the piston 22. As a consequence, the requirement for tolerances is reduced and the tubular member 20 can be made more compact.

Still referring to FIG. 1, it can be seen that the pump 18 comprises a flexible membrane 48. The membrane 48 may alternatively be referred to as a diaphragm. The membrane 48 is fixedly and sealingly attached to the piston rod 24 to follow the linearly reciprocating motion of the piston rod 24. The membrane 48 is also fixedly and sealingly attached with respect to the tubular member 20. Although not illustrated, the membrane 48 may be fixedly and sealingly attached directly to the tubular member 20. The membrane 48 sealingly closes one region (i.e. a part of the right wall in FIG. 1) of the pump 18. In FIG. 1, the membrane 48 is made of PTFE plastics and is therefore also disposable.

Since the piston rod 24 reciprocates linearly with respect to the tubular member 20, the connection between the piston rod 24 and the membrane 48 does not move in a lateral direction (perpendicular to the reciprocating direction) of the piston rod 24. In other words, the lateral forces acting on the membrane 48 during operation of the pump 18 can be reduced or omitted. This opens up for a simpler design (e.g. the possibility to use a weaker membrane 48) and a reduced dimensioning of the membrane 48. The galvanic isolation in the membrane 48 is of course dependent on the provision of a piston rod 24 of non-conductive material.

Due to the configuration of the membrane 48 and the piston rod 24, the risk for contaminants to pass the membrane 48 is reduced or eliminated. Thus, the function of the membrane 48 as a galvanic barrier is improved. The membrane 48 may be said to constitute a second galvanic barrier. Although the pump 18 in FIG. 1 comprising the membrane 48 is disposable, the concept of using the membrane 48 as a galvanic barrier according to the present disclosure may also be employed for medical aspirators 10 with a permanently attached pump 18.

The motor unit 12 in FIG. 1 comprises, in addition to the drive mechanism 40 and the motor 38, also a power distribution unit 50, a control unit 52, a user interface 54 and an ultraviolet light source 56. The power distribution unit 50 may be provided with power from a mains power supply 58. In FIG. 1, the motor unit 12 is implemented as a housing.

The motor unit 12 may be disconnected from the mains power supply 58 in case the medical aspirator 10 is to be carried to a remote location, e.g. to an accidental site distanced from an ambulance. Thus, the mains power supply 58 may be a power supply from a building or a from a vehicle.

The power distribution unit 50 comprises two batteries 60. Each battery 60 is configured to supply drive current to the motor 38 for driving the same. In FIG. 1, the batteries 60 are lead-acid batteries.

The power distribution unit 50 further comprises two relays 62 associated with the respective battery 60. Each relay 62 is switchable between an allowing state and a non-allowing state. In the allowing state of the relay 62, a charge from the mains power supply 58 is allowed to pass to the respective battery 60. In the non-allowing state of the relay 62, a charge from the mains power supply 58 is not allowed to pass to the respective battery 60. The relays 62 are galvanically separated from each other, i.e. an electrical connection therebetween is prevented.

The control unit 52 is an electronic control unit configured to control the two batteries 60 to alternatingly supply drive current to the motor 38. For example, the control unit 52 can send signals to the power distribution unit 50 indicating which of the batteries 60 should provide drive current to the motor 38. The control unit 52 may switch the drive current supplying battery 60 after a predetermined time or when the battery 60 currently driving the motor 38 is discharged or nearly discharged.

Furthermore, by sending control signals to two relays 62 to control their switching states, the control unit 52 is configured to control the relays 62 such that the relay 62 of the battery 60 that currently supplies drive current to the motor 38 adopts the non-allowing state and the relay 62 of the other battery 60 that does not supply drive current to the motor 38 adopts the allowing state. In this manner, the motor 38 is never electrically connected to the mains power supply 58. Thus, the two relays 62 form a third galvanic barrier and the safety for the patient treated by the medical aspirator 10 and for the operator of the medical aspirator 10 is increased.

The battery 60 that is not supplying drive current to the motor 38 and that has its corresponding relay 62 in the allowing state is being charged by the mains power supply 58 (when the medical aspirator 10 is connected to the mains power supply 58). Thus, with this control of the batteries 60 by the control unit 52, one battery 60 supplies a drive current to the motor 38 when the other battery 60 is being charged.

In FIG. 1, the motor 38 is a BLDC motor configured to provide a rotational moment proportional to the drive current. Since the vacuum generated by the vacuum pump 18 is proportional to the drive current of the motor 38, the drive current indicates the generated vacuum. The control unit 52 is configured to control the motor 38 (e.g. via the power distribution unit 50) based on the detected generated vacuum. Thereby, the vacuum generated by the vacuum pump 18 can be controlled in a simple and reliable manner. Additionally, a conventional mechanical vacuum regulator within the medical aspirator 10 can be avoided, or merely used in a complementary manner.

Figure 2A:
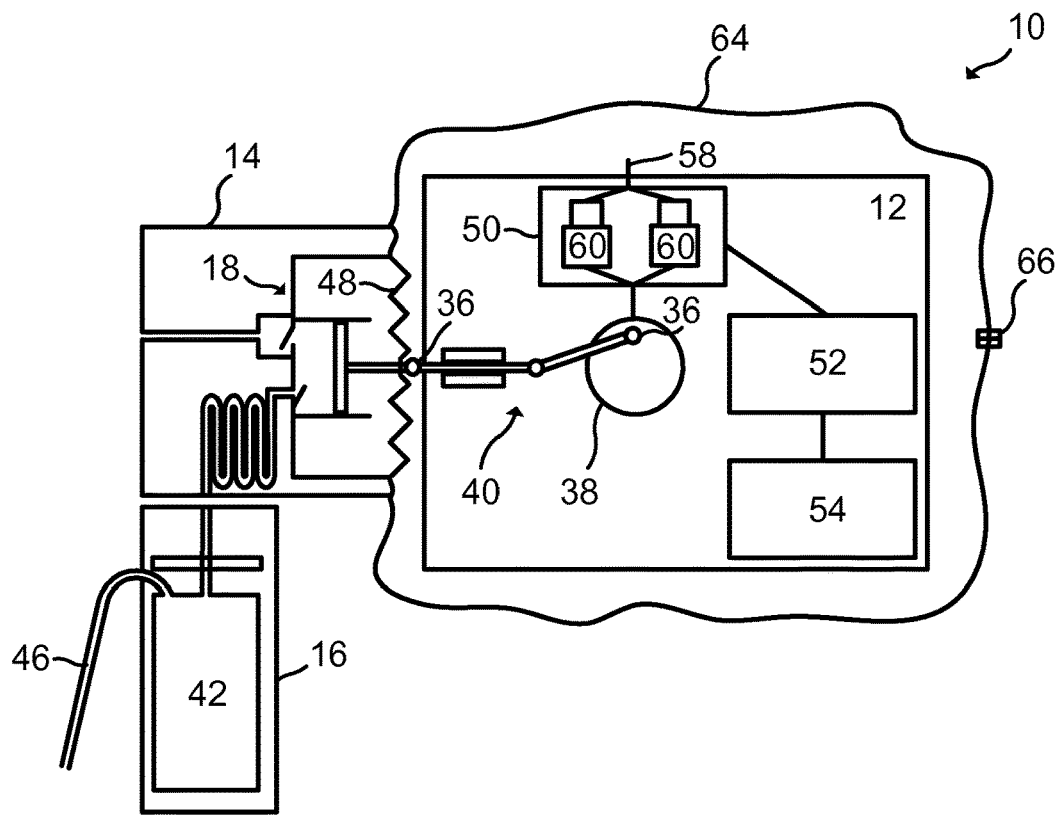
FIG. 2a: schematically represents a medical aspirator with a flexible enclosure covering a motor unit.
Figure 2B:
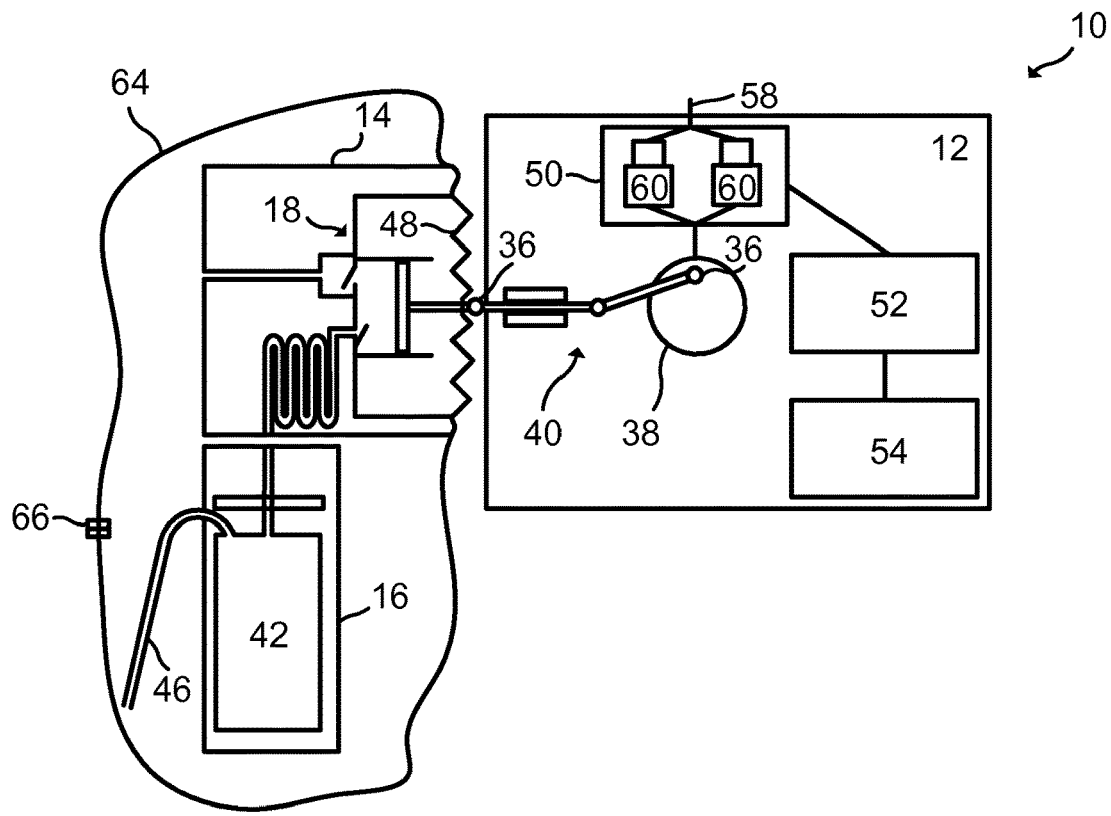
FIG. 2b: schematically represents the medical aspirator in FIG. 2a with the flexible enclosure covering a pump unit.

FIGS. 2a and 2b schematically represent a further medical aspirator 10. Mainly differences with respect to FIG. 1 will be described.

The medical aspirator 10 in FIGS. 2a and 2b comprises a pump unit 14, a canister unit 16 and a motor unit 12. Thus, the pump unit 14 comprises the vacuum pump 18 driven by the motor 38 of the motor unit 12.

The pump unit 14 further comprises a flexible enclosure 64. As can be seen in FIG. 2a, the flexible enclosure 64 is configured to enclose the motor unit 12 and thereby provide a bacterial shield around the motor unit 12 during a suction operation of the medical aspirator 10. Thus, infectious agents in the atmosphere or on the hands/gloves of an operator do not stick directly to the motor unit 12. In FIG. 2a, the flexible enclosure 64 is in a ready mode or operational mode.

After completion of the suction operation, the flexible enclosure 64 can be inverted (i.e. turned "inside-out") to provide a bacterial shield around the pump unit 14, as illustrated in FIG. 2b. In this state, infectious agents previously collected on the outside of the flexible enclosure 64 in the ready mode are thereby collected and trapped within (e.g. on the inside of) the flexible enclosure 64. The state of the flexible enclosure 64 in FIG. 2b is referred to as a disposal mode.

Thus, by inverting or switching the flexible enclosure 64 in this manner, the flexible enclosure 64 may first protect the motor unit 12 in the ready mode (FIG. 2a) and then protect the operator and other personnel involved in logistics and disposal in the disposal mode (FIG. 2b) from infectious agents and/or secretions. The pump unit 14 and the flexible enclosure 64 thereby constitutes a disposable arrangement where the pump unit 14 constitutes a first disposable part and the motor unit 12 constitutes a second part to which the first disposable part is connectable.

The flexible enclosure 64 is described as flexible since it can be inverted, i.e. the flexible enclosure 64 can be bent at some or all regions. The flexible enclosure 64 may or may not stretchable.

As can be seen in FIG. 2b, the flexible enclosure 64 in the disposal mode also provides a bacterial shield around the canister unit 16, in addition to the pump unit 14. Also the aspiration hose 46 of the canister unit 16 is captured within the flexible enclosure 64 in the disposal mode. The operator may also throw used gloves and other waste into the flexible enclosure 64 before closing the same around the pump unit 14 and the canister unit 16.

In the ready mode of the flexible enclosure 64, as illustrated in FIG. 2a, when the flexible enclosure 64 encloses the motor unit 12, the user interface 54 can be operated through the flexible enclosure 64, e.g. by pushing on the flexible enclosure 64.

In case the pump 18 comprises a membrane 48 as described above, the membrane 48 and the flexible enclosure 64 may be integrally formed as one continuous part. The membrane 48 and the flexible enclosure 64 may even be formed from the same material.

In FIGS. 2a and 2b, the flexible enclosure 64 is a plastic bag. The flexible enclosure 64 further comprises a closable opening 66, here implemented as a zip-lock. Thereby, when the opening 66 is in a closed condition, a fluid tight seal is established around the motor unit 12 (in the ready mode) or around the pump unit 14 and the canister unit 16 (in the disposal mode), as the case may be, by the closed opening 66 and the flexible enclosure 64. Since the flexible enclosure 64 is a plastic bag, also corresponding air tight enclosures can be established.

In an open condition, the opening 66 is sufficiently large for the motor unit 12 to pass therethrough and for the pump unit 14 and the canister unit 16 to pass therethrough. Thus, the opening 66 in the open condition allows the flexible enclosure 64 to be inverted from the ready mode to the disposal mode.

Figure 3A:
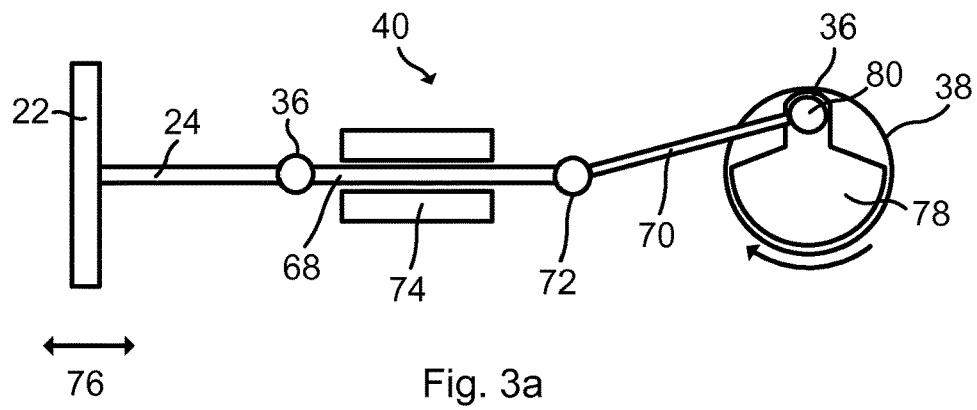
FIG. 3a: schematically represents a drive mechanism.

FIG. 3a schematically represents a drive mechanism 40 for use in a medical aspirator 10 according to the present disclosure. The drive mechanism 40 comprises a first arm 68 and a second arm 70. In FIG. 3a, the arms 68, 70 are constituted by rigid rods. The first arm 68 is pivotally connected to the second arm 70 about a pivot point 72.

The drive mechanism 40 further comprises a guiding arrangement 74. In FIG. 3a, the guiding arrangement 74 is realized as a linear bearing. The guiding arrangement 74 slidingly supports a linearly reciprocating movement of the first arm 68, as indicated with the arrow 76.

In FIG. 3a, the coupling mechanism 36 provides a detachable rigid coupling between the piston rod 24 and the first arm 68. Thus, the piston rod 24 and the first arm 68 move together as a unitary rigid structure.

The motor 38 comprises an eccentric 78 on top of its rotating motor shaft. However, the eccentric 78 may alternatively be separated from this motor shaft, for example by means of an intermediate belt transmission. The second arm 70 in FIG. 3a is rotatably connected to the eccentric 78 at a pivot point 80 offset with respect to the rotational axis of the motor shaft. The second arm 70 thus constitutes an eccentric rod.

As also indicated in FIG. 3a, the coupling mechanism 36 may alternatively be attached between the second arm 70 of the drive mechanism 40 and the eccentric 78. In case the coupling mechanism 36 is provided at this point, the piston rod 24 and the first arm 68 may be integrally formed (i.e. the coupling mechanism 36 between these parts may be omitted) and the drive mechanism 40 may be disposable.

Figure 3B:
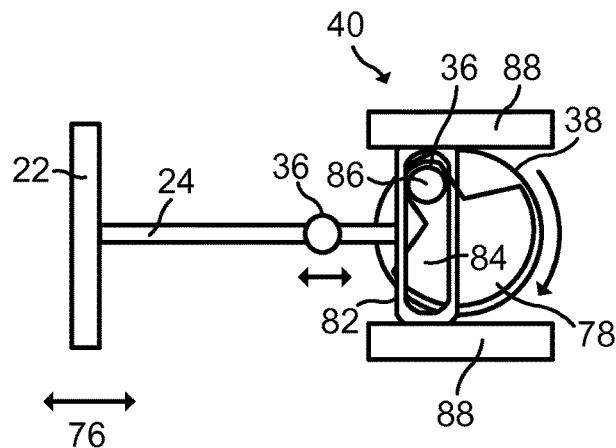
FIG. 3b: schematically represents a further drive mechanism.

FIG. 3b schematically represents a further drive mechanism 40 for use in a medical aspirator 10 according to the present disclosure. Mainly differences with respect to FIG. 3a will be described.

This drive mechanism 40 comprises a track member 82 with a track 84 extending substantially perpendicular to the reciprocating directions 76. A pin 86 is provided on the eccentric 78 and guidingly received in the track 84. The pin 86 is arranged offset on the eccentric 78 with respect to a rotational axis of the motor shaft.

The track member 82 is linearly guided within a frame 88. The frame 88 comprises two inwardly facing grooves (not shown) in which the outer sides of the track member 82 are received.

As can be seen in FIG. 3b, the coupling mechanism 36 may alternatively be provided in the region of the pin 86. Thus, also the track member 82 may be disposable. The track member 82 may be snap-fitted onto the pin 86 and engaged within the frame 88 for driving the pump 18 with the drive mechanism 40. When a suction operation has been completed, the track member 82 may be lifted off the pin 86 and a new track member 82 (of a new pump 18) may be connected thereto. In this case, the coupling mechanism 36 between the piston rod 24 and the track member 82 may be omitted. Thus, the piston rod 24 may be integrally formed with the track member 82.

Figure 4:
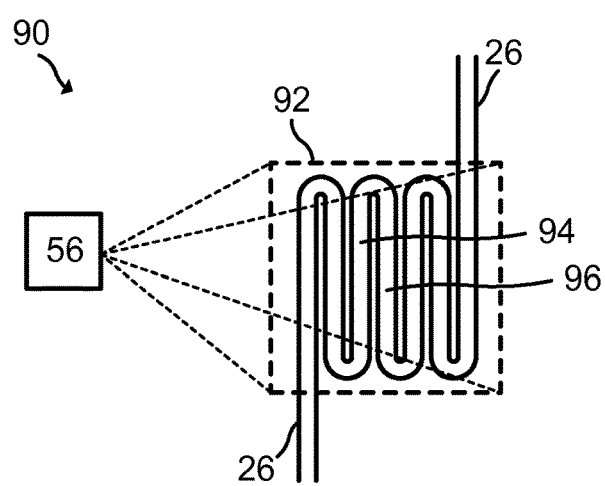
FIG. 4: schematically represents an arrangement for inactivating infectious agents in an air stream.

FIG. 4 schematically represents an arrangement 90 for inactivating infectious agents in an air stream. The arrangement 90 can also be used to inactivate infectious agents in a fluid stream. The air stream may be an air stream within a medical aspirator 10, such as within the vacuum channel 26 in FIG. 1, either within the pump unit 14 or within the canister unit 16.

The arrangement 90 in FIG. 4 thus comprises a channel 26 for guiding an air stream therethrough and further comprises an ultraviolet light source 56 (in FIG. 1, the ultraviolet light source 56 is provided at the exterior of the motor unit 12). The channel 26 is constituted by a material permeable to ultraviolet light, in this case a plastic material. The ultraviolet light source 56 is constituted by a LED light source.

The ultraviolet light source 56 is arranged adjacent to the channel 26 such that ultraviolet light from the light source 56 is directed to a treating section 92 of the channel 26 (indicated by the dashed lines in FIG. 4). The channel 26 is arranged such that a plurality of channel segments 94, guiding the air stream in one direction, and a plurality of channel segments 96, guiding the air stream in a different direction (the opposite direction in this case), are arranged within the treating section 92. The respective channel segments 94, 96 are interconnected with a plurality of bends.

The ultraviolet light source 56 may be configured to provide UV type C (UVC) with a wavelength of 200 to 280 nm, such as a wavelength of 250 to 280 nm, such as 265 nm. Radiation in the UVC-range of 250 to 280 nm deactivates bacteria, viruses and other infectious agents by attacking their DNA.

Each infectious agent requires a specific dose of UVC to be inactivated. The UV dose ($J/m^2$) is calculated by the UV intensity ($mW/cm^2$) multiplied by the exposure time(s). The predictable dose required for a specific degree of disinfection is referred to as a "log reduction", i.e. logarithmic reduction. A 1 log reduction and a 2 log reduction correspond to a 90% and a 99% reduction, respectively, of infectious agents. Each infectious agent is further associated with a specific dose-response curve indicating the required dose to reach various log inactivations.

Since the UV intensity might change (typically decrease) between the light source 56 and the treating section 92, an ultimate UV intensity at the light source may be calculated by taking into account parameters such as the type or types of infectious agents to be inactivated, dose, log reduction, dose-response relationship, velocity of air (or fluid) stream, light source power and spread angle, how the light spreads etc. The goal is to expose the air stream to a sufficient dose to achieve the wanted log reduction results.

With the design according to FIG. 4, the channel 26 is compactly arranged within the treating section 92. Thus, the size of the treating section 92 may be reduced. Furthermore, the exposure to ultraviolet light may be increased since the air stream travels along an elongated distance within the treating section 92. The arrangement of the channel 26 may however also be compactly arranged within the treating section 92 with other designs, including a channel 26 formed as a spiral, coil, helix, or other arbitrary patterns. A wide range of designs may thus be used to expose a large volume of air to UV radiation within a restricted area.

Figure 5A:
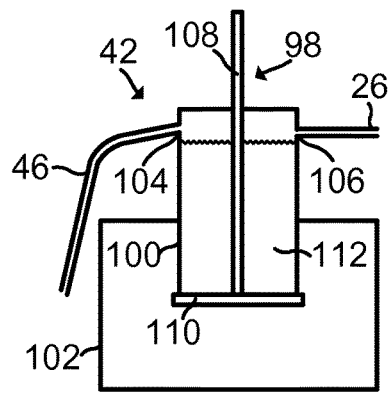
FIG. 5a: schematically represents a two-stage canister with a partition member in a closed position.
Figure 5B:
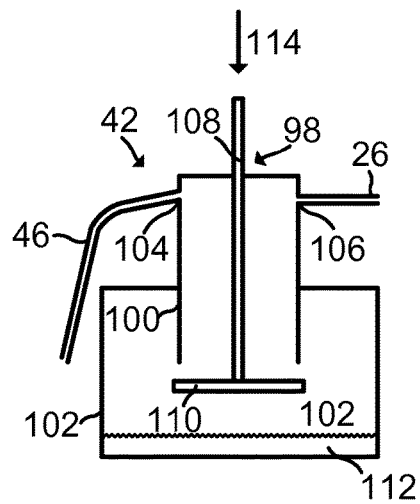
FIG. 5b: schematically represents the two-stage canister in FIG. 5a with the partition member in a drain position.

FIG. 5a schematically represents a two-stage canister 42 with a partition member 98 in a closed position and FIG. 5b schematically represents the two-stage canister 42 in FIG. 5a with the partition member 98 in a drain position.

The canister 42 may be used with a medical aspirator 10 according to the present disclosure. For example, the canister 42 may be comprised in a canister unit 16. The canister unit 16 may be permanently attached or detachably attachable to a pump unit 14.

The two-stage canister 42 comprises a first reservoir 100 and a second reservoir 102, in FIG. 1 implemented as tubular members in the form of two cylinders. The first reservoir 100 and the second reservoir 102 may alternatively be referred to as a first chamber and a second chamber, respectively, or as a first stage canister and a second stage canister, respectively.

The second reservoir 102 has a larger volume than the first reservoir 100. The first reservoir 100 has a volume of approximately 300 ml and the second reservoir 102 has a volume of approximately 700 ml. In this implementation, the first reservoir 100 and the second reservoir 102 are made of disposable plastics.

An aspiration hose 46 and a vacuum channel 26 are attached adjacent to the top of the first reservoir 100. The aspiration hose 46 is attached to an inlet 104 of the first reservoir 100 and the vacuum channel 26 is attached to an outlet 106 of the first reservoir 100. The aspiration hose 46 is used to suction patient secretions into the first reservoir 100 as described above. The vacuum channel 26 is used to establish a vacuum within the first reservoir 100 by means of a pump 18 as described above. A filter (not shown) may be provided in the vacuum channel 26 as also described above.

In FIG. 1, the partition member 98 is implemented as a piston rod 108 with a closing piston 110 with an outer diameter larger than the inner diameter of the first reservoir 100. In the illustrated closed position of the partition member 98, the closing piston 110 sealingly closes the first reservoir 100 to the second reservoir 102 by abutting against the lower rim of the first reservoir 100. Thus, the partition member 98 is configured to maintain a suctioned fluid 112 within the first reservoir 100.

In the closed position of the partition member 98 in FIG. 5a, the second reservoir 102 is functionally isolated from the first reservoir 100 so that when running the pump 18, a vacuum is generated within the first reservoir 100 but not within the second reservoir 102. In other words, the effective volume for vacuum buildup in the two-stage canister is merely constituted by the volume of the first reservoir 100 (approximately 300 ml). Since this effective volume is reduced, the time for establishing a vacuum sufficient to suction fluids and secretions from a patient with the aspiration hose 46 is reduced.

As illustrated in FIG. 5a, the first reservoir 100 has been filled with the fluid 112 suctioned from a patient through the aspiration hose 46. In order to drain the fluid 112 within the first reservoir 100 to the second reservoir 102, the partition member 98 is moved from the illustrated closed position in FIG. 5a to a drain position as illustrated in FIG. 5b. The movement is illustrated with arrow 114 in FIG. 5b. By lowering the closing piston 110 down from the lower rim of the first reservoir 100, a fluid communication between the first reservoir 100 and the second reservoir 102 is established such that the fluid 112 is drained from the first reservoir 100 to the second reservoir 102 by means of gravity.

Since the piston rod 108 extends through the exterior of the first reservoir 100, the part of the piston rod 108 extending outside of the first reservoir 100 can be actuated by an operator to maneuver the partition member 98 from the closed position to the drain position (and in the reverse direction, described later). Thus, the piston rod 108 also constitutes a handle.

The fluid communication is also established between the inlet 104 and the outlet 106 of the first reservoir 100 on the one hand and the second reservoir 102 on the other hand. Thus, when the partition member 98 adopts the drain position as illustrated in FIG. 5b, the effective volume of the two-stage canister in terms of vacuum build-up is constituted by a larger volume, i.e. the volumes of both the first reservoir 100 and the second reservoir 102 (approximately 1000 ml in this implementation).

In this implementation, not only the first reservoir 100, but also the second reservoir 102 is dimensioned to withstand a reduced pressure, i.e. a vacuum build-up. As an example, both the first reservoir 100 and the second reservoir 102 may be made of rigid plastics. Consequently, by maintaining the partition member 98 in the drain position according to FIG. 5b, the two-stage canister 42 can continue to operate as a "one-stage canister". That is, the subsequent suction operation can be carried out with a large continuous volume formed by both the first reservoir 100 and the second reservoir 102.

In case it is not needed to run the two-stage canister 42 again with a reduced volume, it is possible that the partition member 98 is configured to be irreversibly movable from the closed position in FIG. 5a to the drain position in FIG. 5b. This could be useful in order to provide a simple design and/or manufacturing procedure, for example for a disposable two-stage canister 42. As an example, a weak (e.g. plastic) coupling may be provided initially between the first reservoir 100 and the closing piston 110 to hold these parts together, i.e. to maintain the partition member 98 in the closed position. By pushing the piston rod 108 downwardly, the plastic coupling breaks (irreversibly) to allow the partition member 98 to move into the drain position.

This plastic coupling may form a visible seal (in case the second reservoir 102 is made of transparent material). Accordingly, if the visible seal is not broken, it can be assured that no fluid 112 has entered the second reservoir 102. In this case, only the first reservoir 100 may be replaced. The seal may also comprise a material changing colors when contacted by the fluid 112. Thereby, the visual indication of a broken seal can be further improved.

The two-stage canister 42 according to FIGS. 5a and 5b may be operated as follows. With the partition member 98 in the closed position (FIG. 5a), the pump is started to suction fluid 112 into the first reservoir 100. Thus, the two-stage canister 42 is used with a lower volume (only the first reservoir 100).

When the first reservoir 100 is to be drained, the partition member 98 is lowered into the drain position (FIG. 5b) to drain the fluid 112 into the second reservoir 102 by gravity. The pump may continue to run as the second reservoir 102 is being activated. Now, the two-stage canister 42 is used with a higher volume, i.e. the pump now sucks fluids 112 into both the first reservoir 100 and the second reservoir 102. Thus, fluids 112 sucked into the first reservoir 100 continuously drain into the second reservoir 102.

Figure 6A:
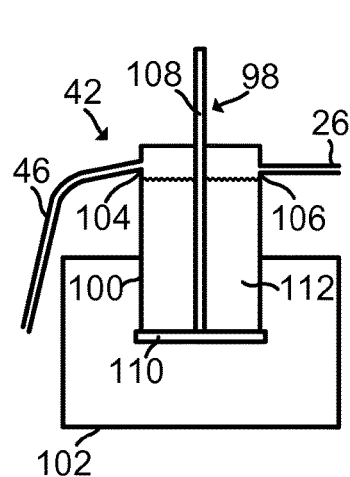
FIG. 6a: schematically represents a further two-stage canister with a partition member in a closed position.
Figure 6B:
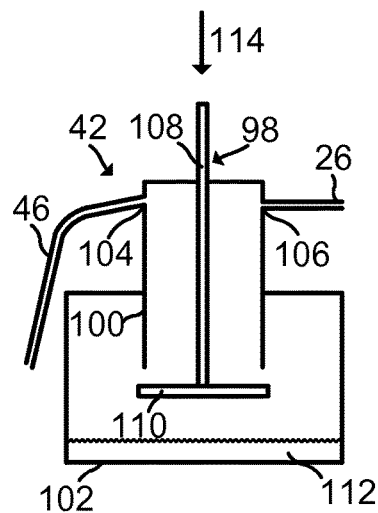
FIG. 6b: schematically represents the two-stage canister in FIG. 6a with the partition member in a drain position.
Figure 6C:
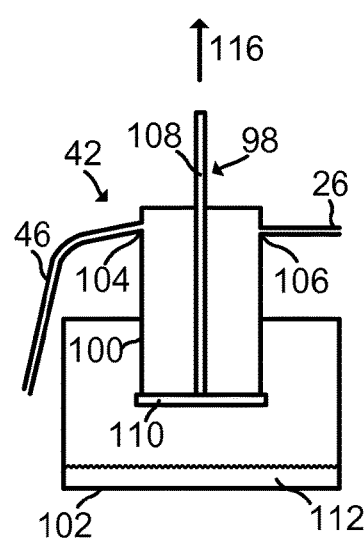
FIG. 6c: schematically represents the two-stage canister in FIGS. 6a and 6b with the partition member again in the closed position.

FIG. 6a schematically represents a further two-stage canister 42 with a partition member 98 in a closed position, FIG. 6b schematically represents the two-stage canister 42 in FIG. 6a with the partition member 98 in a drain position and FIG. 6c schematically represents the two-stage canister 42 in FIGS. 6a and 6b with the partition member 98 again in the closed position. Mainly differences with respect to FIGS. 5a and 5b will be described.

In FIGS. 6a, 6b and 6c, the procedure for draining fluid 112 from the first reservoir 100 to the second reservoir 102 substantially corresponds to the procedure described in connection with FIGS. 5a and 5b. However, as illustrated in FIG. 6c, the partition member 98 is also movable from the drain position in FIG. 6b to the closed position in FIG. 6c. The movement is illustrated with the arrow 116 in FIG. 6c.

For all variants where the partition member 98 is movable from the drain position to the closed position, the partition member 98 may be biased towards the closed position. This may for example be realized with a suitable spring arrangement. Thus, the partition member 98 can be pressed by the operator to move from the closed position to the drain position (direction 114). When the partition member 98 is to move in the opposite direction (direction 116), the partition member 98 can simply be released and the biasing action on the partition member 98 serves to move the same from the drain position to the closed position.

Thus, the partition member 98 is in this implementation reversibly movable between the closed position (FIGS. 6a and 6c) and the drain position (FIG. 6b). Thereby, the two-stage canister 42 can repeatedly run with a reduced volume (i.e. with the partition member 98 in the closed position) with one or several emptying procedures (i.e. with the partition member 98 in the drain position) between the repeated runs.

In case the canister 42 is only run with a reduced volume, the dimensioning of the second reservoir 102 can be reduced (e.g. made of a weaker plastic than the second reservoir 102 in FIGS. 5a and 5b) since the second reservoir 102 does not have to withstand the reduced pressure during vacuum build-up. This opens up for a simpler design and the second reservoir 102 may only be dimensioned to withstand atmospheric pressure.

However, the second reservoir 102 in FIGS. 6a, 6b and 6c may alternatively be made of the same rigid material as the second reservoir 102 in FIGS. 5a and 5b, i.e. dimensioned to withstand vacuum build-up. In this way, the two-stage canister 42 may be repeatedly run with two different effective volumes.

The two-stage canister 42 according to FIGS. 6a, 6b and 6c may be operated as follows. With the partition member 98 in the closed position (FIG. 6a), the pump is started to suction fluid 112 into the first reservoir 100. Thus, the two-stage canister 42 is used with a lower volume (only the first reservoir 100).

When the first reservoir 100 is to be drained, the pump is stopped and the partition member 98 is lowered into the drain position (FIG. 6b) to drain the fluid 112 into the second reservoir 102 by gravity. After draining the fluid 112, the partition member 98 is moved back into the closed position (FIG. 6c), for example by means of the spring arrangement. When the partition member 98 has adopted the closed position, the pump is started anew and a suction cycle with a lower volume (only the first reservoir 100) is started.

Alternatively, after the fluid 112 has been drained into the second reservoir 102, the partition member 98 is maintained in the drain position (FIG. 6b) and the pump is started anew and a suction cycle with a higher volume (with both the first reservoir 100 and the second reservoir 102) is started. In this case, the spring arrangement may be omitted or a locking mechanism for locking the partition member 98 in the drain position may be provided.

Figure 7A:
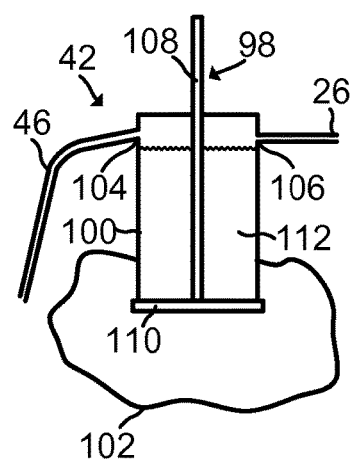
FIG. 7a: schematically represents a further two-stage canister with a partition member in a closed position.
Figure 7B:
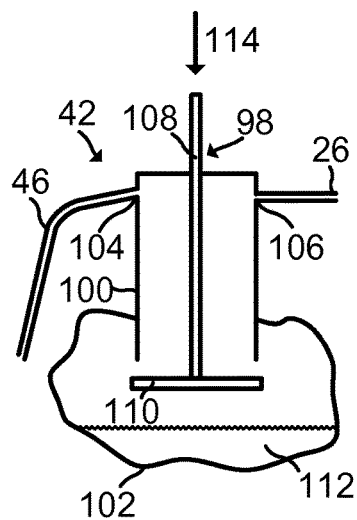
FIG. 7b: schematically represents the two-stage canister in FIG. 7a with the partition member in a drain position.
Figure 7C:
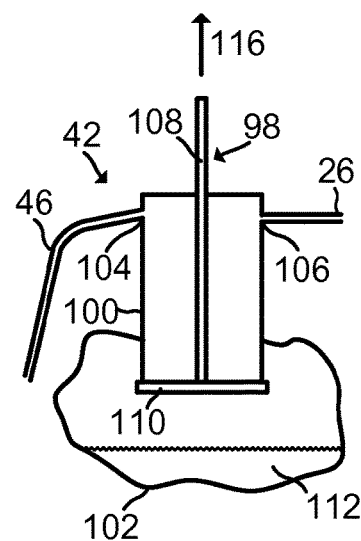
FIG. 7c: schematically represents the two-stage canister in FIGS. 7a and 7b with the partition member again in the closed position.

FIG. 7a schematically represents a further two-stage canister 42 with a partition member 98 in a closed position, FIG. 7b schematically represents the two-stage canister 42 in FIG. 7a with the partition member 98 in a drain position and FIG. 7c schematically represents the two-stage canister 42 in FIGS. 7a and 7b with the partition member 98 again in the closed position. Mainly differences with respect to FIGS. 5a, 5b, 6a, 6b and 6c will be described.

In the implementation of FIGS. 7a, 7b and 7c, the second reservoir 102 is made of a flexible material, such as a soft plastic bag or bellow. The material of the second reservoir 102 may additionally be stretchable.

In the closed position of the partition member 98 as illustrated in FIG. 7a, the second reservoir 102 is empty. Due to the flexibility (and optionally also the stretchability) of the material of the second reservoir 102, the space occupied by the second reservoir 102 can be reduced.

Since the second reservoir 102 is flexible, it is not suitable for withstanding the reduced pressure during vacuum generation. Thus, with the two-stage canister 42 in FIGS. 7a, 7b and 7c, the partition member 98 is held in the closed position during vacuum generation.

After draining the fluid 112 from the first reservoir 100 to the second reservoir 102 by lowering the partition member 98 (in the direction 114), the partition member 98 is raised (in the direction 116) to again adopt the closed position. During vacuum generation inside the first reservoir 100 for the second time, the fluid 112 from the first cycle is kept inside the second reservoir 102 which thereby occupies an increased volume.

The two-stage canister 42 according to FIGS. 7a, 7b and 7c may be operated as follows. With the partition member 98 in the closed position (FIG. 7a), the pump is started to suction fluid 112 into the first reservoir 100. Thus, the two-stage canister 42 is used with a reduced volume (only the first reservoir 100).

When the first reservoir 100 is to be drained, the pump is stopped and the partition member 98 is lowered into the drain position (FIG. 7b) to drain the fluid 112 into the second reservoir 102 by gravity. The second reservoir 102 expands as the fluid 112 enters the same due to the weight of the fluid 112. In addition, when lowering the partition member 98, the closing piston 110 may help expanding the flexible second reservoir 102.

When a new suction cycle is to be started, the partition member 98 is moved from the drain position (FIG. 7b) to the closed position (FIG. 7c). Once the partition member 98 has adopted the closed position to sealingly close the first reservoir 100 to the second reservoir 102, the pump is started again to initiate the next suction cycle.

Figure 8A:
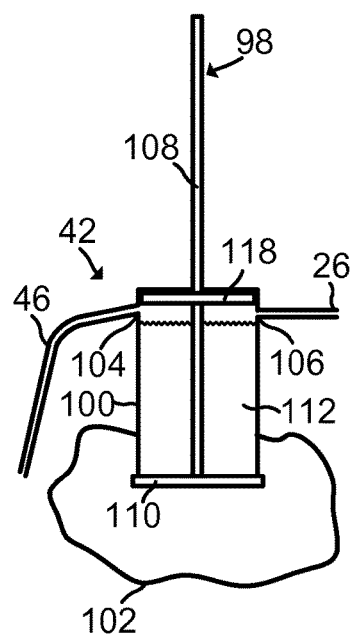
FIG. 8a: schematically represents a further two-stage canister with a partition member in a closed position.
Figure 8B:
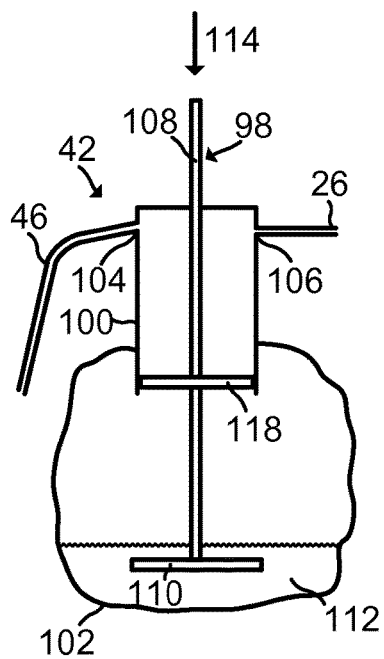
FIG. 8b: schematically represents the two-stage canister in FIG. 8a with the partition member in a drain position.
Figure 8C:
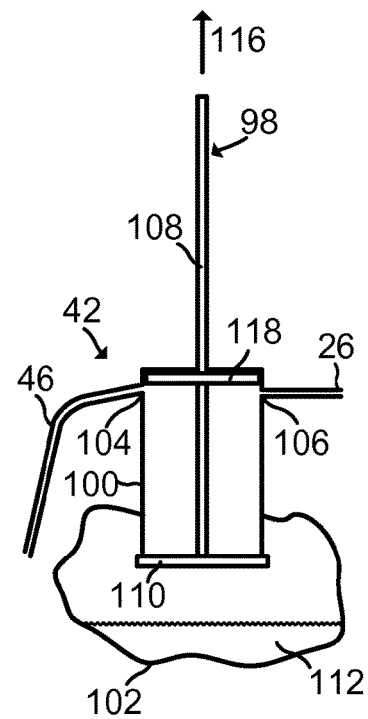
FIG. 8c: schematically represents the two-stage canister in FIGS. 8a and 8b with the partition member again in the closed position.

FIG. 8a schematically represents a further two-stage canister 42 with a partition member 98 in a closed position, FIG. 8b schematically represents the two-stage canister 42 in FIG. 8a with the partition member 98 in a drain position and FIG. 8c schematically represents the two-stage canister 42 in FIGS. 8a and 8b with the partition member 98 again in the closed position. Mainly differences with respect to FIGS. 5a, 5b, 6a, 6b, 6c, 7a, 7b and 7c will be described.

The partition member 98 in FIGS. 8a, 8b and 8c further comprises a pressing piston 118. The pressing piston 118 is provided on the piston rod 108 and is arranged to sealingly slide along the interior surface of the first reservoir 100. As can be seen in FIG. 8a, when the partition member 98 adopts the closed position, the pressing piston 118 is arranged in the upper region of the first reservoir 100 above the inlet 104 and the outlet 106. Thereby, the space formed between the pressing piston 118 and the closing piston 110 inside the first reservoir 100 is subjected to vacuum build-up.

By lowering the partition member 98 in the direction 114 to the drain position as illustrated in FIG. 8b, fluids and secretions 112 inside the first reservoir 100 are pushed down to the second reservoir 102 by the pressing piston 118. Thereby, in case the fluids and secretions 112 do not fall down to the second reservoir 102 by means of gravity, the pressing piston 118 pushes these into the second reservoir 102. In this manner, viscous fluids and/or secretions 112 are more reliably drained into the second reservoir 102. As can be gathered from FIGS. 8a, 8b and 8c, neither in the closed position (FIGS. 8a, 8c), nor in the drain position (FIG. 8b), nor in any intermediate position of the partition member 98 is a fluid communication established between the inlet 104/outlet 106 and the second reservoir 102.

The two-stage canister 42 according to FIGS. 8a, 8b and 8c may be operated as follows. With the partition member 98 in the closed position (FIG. 8a), the pump is started to suction fluid 112 into the first reservoir 100. That is, into the space between the pressing piston 118 and the closing piston 110 inside the first reservoir 100. Thus, the two-stage canister 42 is used with a reduced volume (only the space between the pressing piston 118 and the closing piston 110 within first reservoir 100).

When the first reservoir 100 is to be drained, the pump is stopped and the partition member 98 is lowered into the drain position (FIG. 7b) to drain the fluid 112 into the second reservoir 102 by gravity and simultaneously press fluids/secretions 112 into the second reservoir 102 with the pressing piston 118. The second reservoir 102 expands as the fluid 112 enters the same due to the weight of the fluid 112. In addition, when lowering the partition member 98, the closing piston 110 may help expanding the flexible second reservoir 102.

When a new suction cycle is to be started, the partition member 98 is moved from the drain position (FIG. 8b) to the closed position (FIG. 8c). Once the partition member 98 has adopted the closed position to sealingly close the first reservoir 100 to the second reservoir 102 and once the pressing piston 118 is positioned above the inlet 104 and the outlet 106, the pump is started again to initiate the next suction cycle (with a reduced effective volume). The flexible second reservoir 102 in FIGS. 8a, 8b and 8c may be replaced with a rigid second reservoir 102, e.g. the second reservoir 102 according to FIGS. 6a, 6b and 6c.

Figure 9A:
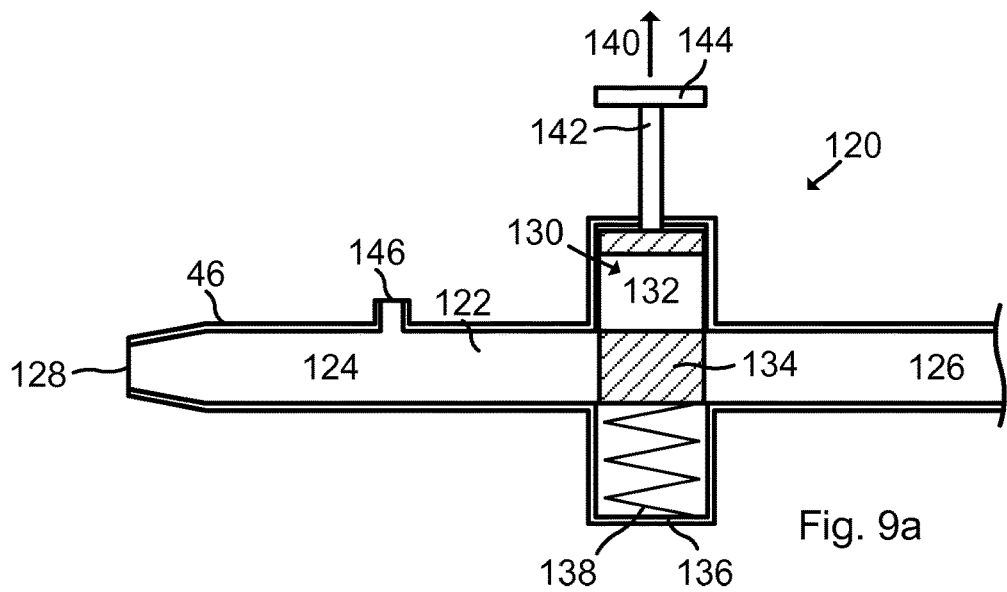
FIG. 9a: schematically represents an aspiration hose with a valve mechanism in a blocking position.
Figure 9B:
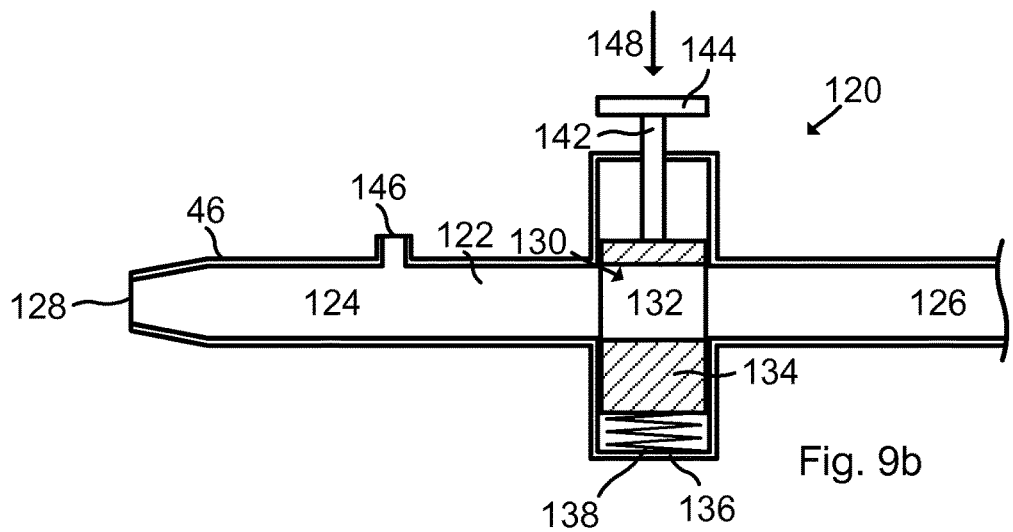
FIG. 9b: schematically represents the aspiration hose in FIG. 9a with the valve mechanism in an open position.
Figure 9C:
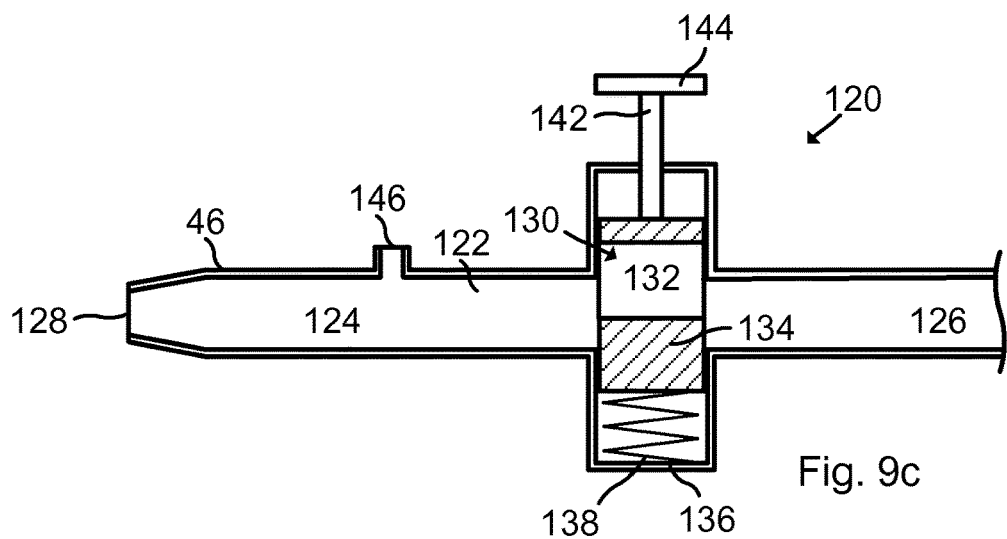
FIG. 9c: schematically represents the aspiration hose in FIGS. 9a and 9b with the valve mechanism in an intermediate position.

FIG. 9a schematically represents an aspiration hose 46 with a valve mechanism 120 in a blocking position, FIG. 9b schematically represents the aspiration hose 46 in FIG. 9a with the valve mechanism 120 in an open position and FIG. 9c schematically represents the aspiration hose 46 in FIGS. 9a and 9b with the valve mechanism 120 in an intermediate position. The aspiration hose 46 in FIGS. 9a, 9b and 9c may be used with any canister 42 and medical aspirator 10 according to the present disclosure to suction bodily fluids and secretions from a patient into the canister 42.

The aspiration hose 46 comprises a main channel 122 through which the suctioned fluids flow. The valve mechanism 120 separates the main channel 122 into an upstream section 124 and a downstream section 126. The upstream section 124 is the section adjacent to a suction opening 128 of the aspiration hose 46 which is brought into contact with or close vicinity to a patient area from which fluids are to be suctioned. The downstream section 126 is permanently fixed or detachably attachable to a canister 42, for example to an inlet 104 as shown in FIGS. 5 to 8.

The valve mechanism 120 in FIG. 9a implemented as comprising a valve member 130 having an opening part 132 and a closing part 134. In the blocking position of FIG. 9a, the closing part 134 of the valve member 130 is aligned with the main channel 122 such that the main channel 122 is blocked. Consequently, fluid in the upstream section 124 is prevented from entering the downstream section 126.

The valve mechanism 120 comprises a valve mechanism housing 136 extending substantially transverse to a longitudinal extension direction of the aspiration hose 46. The valve mechanism housing 136 guides the movement of the valve mechanism 120. More specifically, the valve member 130 of the valve mechanism 120 is arranged inside the valve mechanism housing 136.

A biasing member 138, in FIG. 9a implemented as a compressed spring, may be mounted inside the valve mechanism housing 136 to exert an upward force (in the direction of arrow 140) on the valve member 130 in order to maintain the valve mechanism 120 in the blocking position. Thus, the valve mechanism 120 constitutes a normally-closed valve.

The valve mechanism 120 further comprises a stem 142 extending through an opening in the valve mechanism housing 136 and a button 144 attached on top of the stem 142. An air inlet 146 constituted by an opening is formed in an upper (as seen in FIG. 9a) wall of the aspiration hose 46. However, the air inlet 146 may be provided on alternative sides of the aspiration hose 46, e.g. for being obstructed by a finger other than the thumb. When not obstructed, the air inlet 146 establishes a fluid communication between the upstream section 124 of the aspiration hose 46 and the atmosphere. The air inlet 146 may be intentionally obstructed and cleared by an operator, e.g. with the thumb. For example, the air inlet 146 can be obstructed by the thumb in order to maintain a vacuum within the upstream section 124 and the air inlet 146 can be cleared to release this vacuum if the aspiration hose 46 sticks to patient tissue and the valve mechanism 120 is in the blocking position.

The valve mechanism 120 can be moved from the blocking position in FIG. 9a to the open position in FIG. 9b, for example by pushing down the button 144, as indicated by the arrow 148. Thus, the valve mechanism 120 is switchable between the blocking position and the open position. By pushing down the button 144, the valve member 130 moves down inside the valve mechanism housing 136 until the opening part 132 is aligned with the main channel 122 of the aspiration hose 46. Thereby, the upstream section 124 is brought into fluid communication with the downstream section 126. In other words, the valve mechanism 120 in the open position allows fluid to pass from the upstream section 124 to the downstream section 126 of the aspiration hose 46. A locking mechanism (not shown) may be provided to lock the valve mechanism 120 in the open position illustrated in FIG. 9b.

FIG. 9c illustrates the valve mechanism 120 in an intermediate position, between the blocking position in FIG. 9a and the open position in FIG. 9b. As can be seen in FIG. 9c, when the valve mechanism 120 adopts this intermediate position, the valve member 130 is positioned such that its opening part 132 is offset with respect to the main channel 122. Thereby, the fluid communication between the upstream section 124 and the downstream section 126 is partly restricted. With the valve mechanism 120 according to FIGS. 9a, 9b and 9c, the valve member 130 of the valve mechanism 120 can accomplish any restriction (from full restriction to no restriction) to the main channel 122 by moving the valve member 130 inside the valve member housing 136. That is, a plurality of intermediate positions can be adopted by the valve mechanism 120.

Figure 10A:
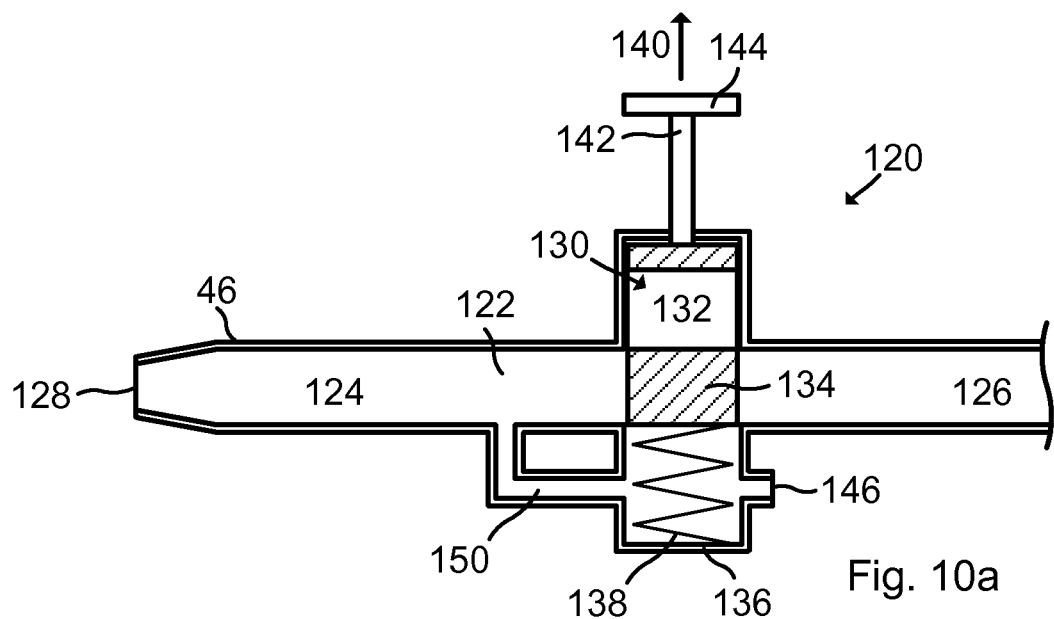
FIG. 10a: schematically represents a further aspiration hose with a valve mechanism in a blocking position.
Figure 10B:
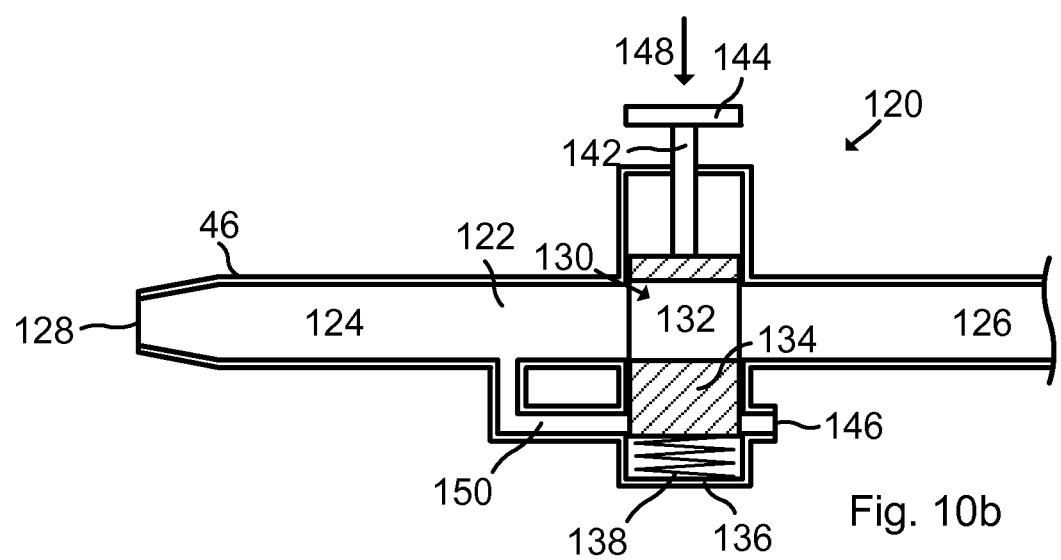
FIG. 10b: schematically represents the aspiration hose in FIG. 10a with the valve mechanism in an open position.

FIG. 10a schematically represents a further aspiration hose 46 with a valve mechanism 120 in a blocking position and FIG. 10b schematically represents the aspiration hose 46 in FIG. 10a with the valve mechanism 120 in an open position. Mainly differences with respect to FIGS. 9a, 9b and 9c will be described.

Instead of the air inlet 146 according to FIGS. 9a, 9b and 9c, the valve mechanism 120 in FIG. 10a comprises an air inlet channel 150 between the upstream section 124 and the atmosphere through the valve mechanism housing 136. In FIG. 10a, the air inlet channel 150 is led through the lower part of the valve mechanism housing 136 where the biasing member 138 is provided. The air inlet channel 150 ends with an air inlet 146.

In the blocking position of the valve mechanism 120 in FIG. 10a, the closing part 134 is raised above the air inlet channel 150. Thus, the air inlet channel 150 is only negligibly obstructed by the biasing member 138. Thus, when the valve mechanism 120 adopts the blocking position, the upstream section 124 is in communication with the atmosphere, but not with the downstream section 126.

When the valve mechanism 120 is maneuvered from the blocking position in FIG. 10a to the open position in FIG. 10b, the opening part 132 of the valve member 130 is moved into alignment with the main channel 122 and the upstream section 124 is consequently brought into fluid communication with the downstream section 126. At the same time, the closing part 134 of the valve member 130 is moved from alignment with the main channel 122 and into a lower position within the valve mechanism housing 136 where it blocks the air inlet channel 150 such that communication between the atmosphere and the upstream section 124 is prevented. In other words, the valve mechanism 120 is configured such that fluid communication between the upstream section 124 and the atmosphere is closed when the valve mechanism 120 adopts the open position.

The aspiration hose 46 in FIGS. 9a, 9b, 9c, 10a and 10b may be operated as follows. With a method for controlling the vacuum generated by a vacuum pump 18 driven by a motor 38 in a medical aspirator 10 as described herein, the pump 18 will stop when a desired vacuum set point is reached. Thus, when the valve mechanism 120 adopts the blocking position, the level of vacuum inside the downstream section 126 of the aspiration hose 46 will increase until a target vacuum level is reached.

When the target vacuum level is reached, the pump 18 will stop. Thus, the aspiration hose 46 may be brought to the vicinity of a patient with the valve mechanism 120 in the blocking position and the motor 38 turned off.

As the medical suction operation is to be initiated, the operator actuates the valve mechanism 120, e.g. by pushing the button 144 downwardly in the direction 148. As soon as the opening part 132 of the valve member 130 establishes a fluid communication between the upstream section 124 and the downstream section 126, air (and/or fluids) inside the upstream section 124 will move into the downstream section 126. Since the vacuum level inside the downstream section 126 is thereby decreased, the vacuum pump 18 will be activated to re-establish the target vacuum level.

The operator can adjust the airflow through the aspiration hose 46 by moving the valve mechanism 120 between the blocking position, the open position and any intermediate position. Thus, the valve mechanism 120 is used as an on/off actuator for the vacuum pump 18. In case the aspiration hose 46 according to FIGS. 9a, 9b and 9c is used, the operator may simultaneously obstruct the air inlet 146 with the thumb in order to maintain the vacuum inside the upstream section 124. This function may however also be controlled with the valve mechanism 120, as exemplified in FIGS. 10a and 10b.

In case the suction opening 128 sticks to the patient, the operator can remove the thumb from the air inlet 146 in FIGS. 9a, 9b and 9c. In case the valve mechanism 120 in FIGS. 10a and 10b is used, a deactivation of the valve mechanism 120 (e.g. pressure relief on the button 144) brings the upstream section 124 in communication with the atmosphere such that vacuum inside the upstream section 124 is relieved and the suction opening 128 can easily be removed from a target site of the patient.

The present disclosure provides the following itemized listing of embodiments:

1. Vacuum pump (18) for a medical aspirator (10), the pump (18) comprising:
   a tubular member (20);
   a piston (22) slidably arranged within the tubular member (20);
   a piston rod (24) connected to the piston (22); and
   a coupling mechanism (36) for detachably and functionally connecting the piston rod (24) to a motor (38) for driving the pump (18), wherein the piston rod (24) is configured to reciprocate linearly during operation of the pump (18).

2. The vacuum pump (18) according to item 1, further comprising a drive mechanism (40) configured to translate a rotary motion of the motor (38) to the linearly reciprocating motion of the piston rod (24) and wherein the coupling mechanism (36) is provided on the drive mechanism (40).

3. The vacuum pump (18) according to item 1 or 2, further comprising a membrane (48) fixed to the piston rod (24) for sealingly closing the pump (18).

4. Vacuum pump (18) for a medical aspirator (10), the pump (18) comprising:
   a tubular member (20);
   a piston (22) slidably arranged within the tubular member (20);
   a piston rod (24) connected to the piston (22); and
   a membrane (48) fixed to the piston rod (24) for sealingly closing the pump (18), wherein the piston rod (24) is configured to reciprocate linearly during operation of the pump (18).

5. Motor unit (12) for a medical aspirator (10), the motor unit (12) comprising:
   a motor (38) for driving a vacuum pump (18);
   at least two batteries (60), where each battery (60) is configured to supply drive current to the motor (38);
   a relay (62) associated with each battery (60), wherein each relay (62) is configured to operate between an allowing state for receiving a charge from a mains power supply (58), and a non-allowing state in which the charge from the mains power supply (58) is not allowed.

6. The motor unit (12) according to item 5, wherein the relays (62) of the batteries (60) are galvanically separated from each other.

7. The motor unit (12) according to item 5 or 6, further comprising a control unit (52) configured to control the at least two batteries (60) to alternatingly supply drive current to the motor (38).

8. The motor unit (12) according to item 7, wherein the control unit (52) is configured to alternatingly control the relays (62) such that the relay (62) of the battery (60) that currently supplies drive current to the motor (38) adopts the non-allowing state and the relay (62) of each one or more remaining batteries (60) adopt the allowing state so that the motor (38) is never electrically connected to the mains power supply (58).

9. Medical aspirator (10) comprising a vacuum pump (18) according to any of items 1 to 4 and/or a motor unit (12) according to any of items 5 to 8.

10. Disposable arrangement comprising:
    a first disposable part connectable to a second part, or forming a joint structure together with the second part;
    a flexible enclosure (64) configured to provide a protective shield around the second part during use of the first disposable part together with the second part, and configured to be inverted to provide a protective shield around the first disposable part after completion of the use.

11. The disposable arrangement according to item 10, wherein the flexible enclosure (64) is a plastic bag.

12. The disposable arrangement according to item 10 or 11, wherein the flexible enclosure (64) comprises a closable opening (66) which in an open condition allows the flexible enclosure (64) to be inverted from a state enclosing the second part to a state enclosing the first disposable part and which in a closed condition forms a part of a substantially fluid tight seal around the second part and the first disposable part, respectively.

13. The disposable arrangement according to item 12, wherein the closable opening (66) is constituted by a zip-lock.

14. The disposable arrangement according to any of items 10 to 13, wherein:
    the first disposable part is constituted by a pump unit (14) with a vacuum pump (18) for a medical aspirator (10);
    the second part is constituted by a motor unit (12) with a motor (38) for the medical aspirator (10), where the vacuum pump (18) is drivable by the motor (38); and
    the flexible enclosure (64) is configured to provide a bacterial shield around the motor unit (12) during a suction operation of the medical aspirator (10), and configured to be inverted to provide a bacterial shield around the pump unit (14) after completion of the suction operation of the medical aspirator (10).

15. The disposable arrangement according to item 14, wherein the vacuum pump (18) comprises a membrane (48) and the flexible enclosure (64) is integrally formed with the membrane (48).

16. Medical aspirator (10) comprising:
    a disposable arrangement according to item 14 or 15; and
    a motor unit (12) comprising a motor (38) for driving the vacuum pump (18) of the pump unit (14).

17. The medical aspirator (10) according to item 16, wherein the pump unit (14) is detachably connectable to the motor unit (12).

18. An arrangement (90) for inactivating infectious agents in an air stream, such as an air stream within a medical aspirator (10), the arrangement (90) comprising:
    a channel (26) for guiding an air stream therethrough, the channel (26) being at least partly constituted by a material permeable to ultraviolet light;
    an ultraviolet light source (56) arranged adjacent to the channel (26) configured to expose the air stream within a treating section (92) of the channel (26) to ultraviolet light.

19. The arrangement (90) according to item 18, wherein the channel (26) within the treating section (92) comprises at least two channel segments (94, 96) configured to direct the air stream in different directions.

20. The arrangement (90) according to item 18 or 19, wherein the channel (26) within the treating section (92) is arranged as a spiral, coil or helix and/or comprises a plurality of substantially parallel channel segments (94, 96).

21. Medical aspirator (10) comprising an arrangement (90) according to any of items 18 to 20.

22. Method for controlling the vacuum generated by a vacuum pump (18) driven by a motor (38) in a medical aspirator (10), the method comprising:
    detecting the generated vacuum; and
    controlling the drive current supplied to the motor (38) based on the detected generated vacuum.

23. Medical aspirator (10) comprising:
    a vacuum pump (18);
    a motor (38) configured to drive the vacuum pump (18);
    means for detecting the generated vacuum; and
    a control unit (52) configured to control the drive current supplied to the motor (38) according to the method in item 22.

24. Two-stage canister (42) for a medical aspirator (10), the canister (42) comprising:
    a first reservoir (100) with an inlet (104) for an aspiration hose (46) and an outlet (106) for a vacuum channel (26);
    a second reservoir (102); and
    a partition member (98) movable from a closed position, where the partition member (98) is configured to maintain a fluid (112) within the first reservoir (100), to a drain position in order to drain the fluid (112) within the first reservoir (100) to the second reservoir (102).

25. The two-stage canister (42) according to item 24, wherein both the first reservoir (100) and the second reservoir (102) are configured to withstand a reduced pressure during operation of the two-stage canister (42) with the partition member (98) in the drain position.

26. The two-stage canister (42) according to item 24, wherein the second reservoir (102) is flexible.

27. The two-stage canister (42) according to any of items 24 to 26, wherein the partition member (98) is movable from the drain position to the closed position.

28. The two-stage canister (42) according to any of items 24 to 27, wherein the partition member (98) comprises a closing piston (110) for sealingly closing the first reservoir (100) to the second reservoir (102) when the partition member (98) is in the closed position.

29. The two-stage canister (42) according to item 28, wherein the partition member (98) comprises a piston rod (108) attached to the closing piston (110) and the piston rod (108) extends through the exterior of the first reservoir (100).

30. The two-stage canister (42) according to item 28 or 29, wherein the partition member (98) comprises a pressing piston (118) for pressing the fluid (112) within the first reservoir (100) to the second reservoir (102) during movement of the partition member (98) from the closed position to the drain position.

31. Medical aspirator (10) comprising a two-stage canister (42) according to any of items 24 to 30.

32. Aspiration hose (46) for suctioning fluids from a patient into a canister (42) of a medical aspirator (10), the aspiration hose (46) comprising:
    an upstream section (124);
    a downstream section (126); and a valve mechanism (120) switchable between an open position and a blocking position, wherein the valve mechanism (120) is configured to allow the suctioned fluids to pass from the upstream section (124) to the downstream section (126) in the open position, and to block the suctioned fluids in the upstream section (124) from entering the downstream section (126) in the blocking position.

33. The aspiration hose (46) according to item 32, further comprising a biasing member (138) configured to bias the valve mechanism (120) into the blocking position.

34. The aspiration hose (46) according to item 32 or 33, further comprising an air inlet (146) for fluid communication between the upstream section (124) and the atmosphere when the valve mechanism (120) adopts the blocking position.

35. The aspiration hose (46) according to item 34, wherein the aspiration hose (46) is configured such that fluid communication between the upstream section (124) and the atmosphere is closed when the valve mechanism (120) adopts the open position.

36. Canister (42) comprising an aspiration hose (46) according to any of items 32 to 35.

37. Medical aspirator (10) comprising an aspiration hose (46) according to any of items 32 to 35 or a canister (42) according to item 36.

While the present disclosure has been described with reference to exemplary embodiments, it will be appreciated that the present invention is not limited to what has been described above. For example, it will be appreciated that the dimensions of the parts may be varied as needed. Accordingly, it is intended that the present invention may be limited only by the scope of the claims appended hereto.

The invention claimed is:

1. A motor unit for a medical aspirator, the motor unit comprising:
    a motor for driving a vacuum pump;
    at least two batteries, wherein each battery is configured to supply drive current to the motor; and
    a relay associated with each battery, wherein each relay is configured to operate between:
        an allowing state for receiving a charge from a mains power supply, and
        a non-allowing state in which the charge from the mains power supply is not allowed;
    wherein the control unit is configured to alternatingly control the relays such that the relay of the battery that currently supplies drive current to the motor adopts the non-allowing state and the relay of each one or more remaining batteries adopt the allowing state so that the motor is never electrically connected to the mains power supply.

2. The motor unit according to claim 1, wherein the relays of the batteries are galvanically separated from each other.

3. The motor unit according to claim 1, further comprising a control unit configured to control the at least two batteries to alternatingly supply drive current to the motor.

4. A medical aspirator comprising a motor unit according to claim 1.

5. An arrangement for inactivating infectious agents in an air stream, such as an air stream within a medical aspirator, the arrangement comprising:
    a channel for guiding an air stream therethrough, the channel being at least partly constituted by a material permeable to ultraviolet light; and
    an ultraviolet light source arranged adjacent to the channel configured to expose the air stream within a treating section of the channel to ultraviolet light;
    wherein the channel within the treating section comprises at least two channel segments configured to direct the air stream in different directions.

6. The arrangement according to claim 5, wherein the channel within the treating section is arranged as a spiral, coil or helix and/or comprises a plurality of substantially parallel channel segments.

7. A medical aspirator comprising an arrangement according to claim 5.

* * * * *